(12) United States Patent
Ornelas Vargas et al.

(10) Patent No.: US 11,413,433 B2
(45) Date of Patent: Aug. 16, 2022

(54) DEVICE AND METHOD FOR SINGLE-HANDED ACCESS AND INSERTION OF AN ARTICLE

(71) Applicant: Acantha Medical, LLC, The Woodlands, TX (US)

(72) Inventors: Andres Ornelas Vargas, Mexico City (MX); Brandon James Hudik, Bordentown, NJ (US); Jason Chin, New Haven, CT (US); Blake Thomson, Franklin, TN (US)

(73) Assignee: Acantha Medical, LLC, The Woodlands, TX (US)

( * ) Notice: Subject to any disclaimer, the term of this patent is extended or adjusted under 35 U.S.C. 154(b) by 454 days.

(21) Appl. No.: 15/868,841

(22) Filed: Jan. 11, 2018

(65) Prior Publication Data

US 2018/0126126 A1 May 10, 2018

Related U.S. Application Data

(63) Continuation-in-part of application No. 15/489,683, filed on Apr. 17, 2017.

(60) Provisional application No. 62/447,037, filed on Jan. 17, 2017, provisional application No. 62/323,767, filed on Apr. 17, 2016.

(51) Int. Cl.
| | |
|---|---|
| *A61M 25/09* | (2006.01) |
| *A61M 39/10* | (2006.01) |
| *A61B 17/34* | (2006.01) |
| *A61M 39/22* | (2006.01) |
| *A61M 25/06* | (2006.01) |

(52) U.S. Cl.
CPC ... *A61M 25/09041* (2013.01); *A61B 17/3468* (2013.01); *A61M 39/10* (2013.01); *A61B 17/3403* (2013.01); *A61M 25/0662* (2013.01); *A61M 39/22* (2013.01); *A61M 2025/091* (2013.01)

(58) Field of Classification Search
CPC .... A61M 2025/0003; A61M 2025/091; A61M 2205/3344; A61M 2205/586; A61M 25/0606; A61M 25/0662; A61M 25/09041; A61M 39/10; A61M 39/22; A61B 17/3403; A61B 17/3468
See application file for complete search history.

(56) References Cited

U.S. PATENT DOCUMENTS

| | | | |
|---|---|---|---|
| 4,274,408 A | | 6/1981 | Nimrod |
| 4,351,334 A | * | 9/1982 | Inglefield, Jr. ...... A61M 5/3148 604/227 |
| 4,464,171 A | | 8/1984 | Garwin |
| 4,594,073 A | * | 6/1986 | Stine .................. A61B 10/0283 604/187 |
| 4,813,938 A | | 3/1989 | Raulerson |
| 4,935,008 A | | 6/1990 | Lewis, Jr. |

(Continued)

*Primary Examiner* — Quynh-Nhu H. Vu
(74) *Attorney, Agent, or Firm* — McAughan Deaver PLLC

(57) ABSTRACT

An insertion apparatus for inserting an object into a body comprising a housing, a piercing structure with a lumen, wherein the piercing structure extends distally from the housing, a vacuum chamber that communicates with the lumen of the piercing structure, a plunger configured to fit within the vacuum chamber, a guidewire, and a pressure monitoring channel communicating with the lumen, wherein the insertion apparatus is configured to be operated with a single hand.

20 Claims, 26 Drawing Sheets

(56) References Cited

U.S. PATENT DOCUMENTS

| | | | |
|---|---|---|---|
| 5,125,906 A | 6/1992 | Fleck | |
| 5,241,968 A * | 9/1993 | Slater | A61B 17/29 |
| | | | 600/564 |
| 5,242,414 A | 9/1993 | Fischell et al. | |
| 5,263,938 A | 11/1993 | Orr et al. | |
| 5,279,573 A | 1/1994 | Klosterman | |
| 5,338,311 A | 8/1994 | Mahurkar | |
| 5,366,444 A * | 11/1994 | Martin | A61M 25/09041 |
| | | | 242/405 |
| 5,415,177 A | 5/1995 | Zadini et al. | |
| 5,469,860 A * | 11/1995 | De Santis | A61B 10/0283 |
| | | | 600/562 |
| 5,484,419 A | 1/1996 | Fleck | |
| 5,507,300 A | 4/1996 | Mukai et al. | |
| 5,514,100 A | 5/1996 | Mahurkar | |
| 5,579,780 A | 12/1996 | Zadini et al. | |
| 5,685,862 A | 11/1997 | Mahurkar | |
| 5,730,150 A * | 3/1998 | Peppel | A61M 25/09041 |
| | | | 600/585 |
| 5,749,371 A | 5/1998 | Zadini et al. | |
| 5,827,202 A * | 10/1998 | Miraki | A61M 25/09041 |
| | | | 600/585 |
| 5,830,152 A * | 11/1998 | Tao | A61B 10/0233 |
| | | | 600/562 |
| 5,843,002 A | 12/1998 | Pecor et al. | |
| 5,843,091 A | 12/1998 | Holsinger et al. | |
| 5,879,338 A | 3/1999 | Mahurkar | |
| 5,891,105 A | 4/1999 | Mahurkar | |
| 6,371,944 B1 * | 4/2002 | Liu | A61M 25/06 |
| | | | 604/284 |
| 6,398,743 B1 | 6/2002 | Halseth et al. | |
| 6,547,762 B1 | 4/2003 | Botich et al. | |
| 6,551,281 B1 | 4/2003 | Raulerson et al. | |
| 6,626,869 B1 * | 9/2003 | Bint | A61M 25/09041 |
| | | | 604/158 |
| 6,786,875 B2 | 9/2004 | Barker et al. | |
| 7,048,696 B2 | 5/2006 | Eberhart et al. | |
| 7,153,276 B2 | 12/2006 | Barker et al. | |
| 7,357,787 B2 | 4/2008 | Moss | |
| 7,470,254 B2 | 12/2008 | Basta et al. | |
| 7,611,474 B2 | 11/2009 | Hibner et al. | |
| 7,708,721 B2 | 5/2010 | Khaw | |
| 7,753,887 B2 | 7/2010 | Botich et al. | |
| D622,132 S | 8/2010 | DeMars et al. | |
| 7,771,370 B2 | 8/2010 | Eberhart et al. | |
| 7,857,770 B2 | 12/2010 | Raulerson et al. | |
| 8,251,923 B2 | 8/2012 | Carrez et al. | |
| 8,454,536 B2 | 6/2013 | Raulerson et al. | |
| 8,585,651 B2 | 11/2013 | Asai | |
| 8,915,884 B2 | 12/2014 | Tal | |
| 8,932,258 B2 | 1/2015 | Blanchard et al. | |
| 8,945,092 B1 | 2/2015 | Call et al. | |
| 9,011,351 B2 | 4/2015 | Hoshinouchi | |
| 9,095,683 B2 | 8/2015 | Hall et al. | |
| 9,439,653 B2 | 9/2016 | Avneri et al. | |
| 9,545,504 B2 | 1/2017 | Hoshinouchi | |
| 2003/0036712 A1 | 2/2003 | Heh et al. | |
| 2003/0109808 A1 | 6/2003 | Takinami et al. | |
| 2004/0143219 A1 | 7/2004 | Lee et al. | |
| 2004/0171988 A1 * | 9/2004 | Moretti | A61M 25/09041 |
| | | | 604/164.01 |
| 2008/0319387 A1 | 12/2008 | Amisar et al. | |
| 2011/0152836 A1 | 6/2011 | Riopelle et al. | |
| 2012/0245624 A1 | 9/2012 | Glazier et al. | |
| 2012/0330184 A1 * | 12/2012 | Mahapatra | A61B 17/3401 |
| | | | 600/561 |
| 2013/0096428 A1 | 4/2013 | Gillies et al. | |
| 2013/0281787 A1 | 10/2013 | Avneri et al. | |
| 2013/0331734 A1 | 12/2013 | Keast et al. | |
| 2014/0094774 A1 | 4/2014 | Blanchard | |
| 2014/0128910 A1 | 5/2014 | Glazier et al. | |
| 2014/0296868 A1 * | 10/2014 | Garrison | A61M 5/3137 |
| | | | 606/127 |
| 2015/0119806 A1 | 4/2015 | Blanchard et al. | |
| 2015/0119852 A1 | 4/2015 | Wexler | |
| 2015/0224287 A1 | 8/2015 | Bian et al. | |
| 2015/0231364 A1 | 8/2015 | Blanchard et al. | |
| 2015/0290431 A1 | 10/2015 | Hall et al. | |
| 2015/0352318 A1 | 12/2015 | Almansour et al. | |
| 2016/0067453 A1 | 3/2016 | Braithwaite et al. | |
| 2016/0121086 A1 | 5/2016 | Castro et al. | |
| 2016/0184557 A1 | 6/2016 | Call et al. | |
| 2016/0256667 A1 | 9/2016 | Ribelin et al. | |
| 2016/0331938 A1 | 11/2016 | Blanchard et al. | |
| 2017/0049991 A1 | 2/2017 | Avneri et al. | |

\* cited by examiner

DEVICE AND METHOD FOR SINGLE-HANDED ACCESS AND INSERTION OF AN ARTICLE

CROSS REFERENCE TO RELATED APPLICATIONS

This is a continuing application of, and claims benefit and priority to, U.S. Non-Provisional application Ser. No. 15/489,683, filed on Apr. 17, 2017, and PCT Application Serial No. PCT/US17/28017 also filed on Apr. 17, 2017. This application is related to and claims priority to U.S. Provisional Patent Application Ser. No. 62/323,767, filed on Apr. 17, 2016, and U.S. Provisional Patent Application Ser. No. 62/447,037, filed on Jan. 17, 2017. The complete and entire disclosures of each of which are hereby expressly incorporated by reference herein.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The inventions disclosed and taught herein relate generally to a device and method for the insertion of an article into a body using a single hand; and more specifically relate to the single-handed insertion of a guidewire or similar article or another elongated article such as, for instance, certain catheters into a targeted body space. In particular, the inventions disclosed herein relate to an apparatus that combines insertion of a substantially hollow piercing structure, such as a needle, a suction apparatus, and a guidewire, where the apparatus is configured to use with a single hand, and methods of using such apparatus.

The Seldinger technique is a ubiquitous maneuver in the field of medicine used to safely insert a cannula into a vessel, hollow organ, or body cavity. Examples of procedures and settings where it may be employed include arterial line placements, central venous catheter placements, angiograms, percutaneous tracheostomies, pleural catheter placement, percutaneous cholecystectomy, percutaneous nephrostomy, and percutaneous abscess drainage. With respect to vascular access, it is the current standard of care for placing a catheter, sheath, or cannula into a blood vessel during access procedures such as central venous catheter placement. In applying the Seldinger Technique, a physician first uses a needle to pierce through tissue to ultimately reach a targeted body space. A wire is then passed through the needle into the space. The wire secures a path into the space over which the needle may then be removed and additional instruments such as sheaths and catheters may be inserted into the space.

With respect to central venous catheter insertion and procedures targeting lumens with similarly low-pressure fluids like blood in the venous system, a syringe is coupled to the needle to apply suction. Once the physician gains access to the targeted body space, which is confirmed when a specific body fluid is aspirated into the syringe barrel, the physician holds the hub of the needle with one hand and uncouples the syringe with from the needle with the remaining hand. Once the uncoupling is complete, the physician inserts a guidewire through the lumen of the needle into the targeted body space in order to secure access. The physician then removes the needle, nicks the skin with a scalpel, and passes a dilator over the guidewire to dilate the tissue around the guidewire in order to facilitate catheter, sheath, or cannula insertion. Once the dilator is withdrawn, the physician passes the catheter, sheath, or cannula over the guidewire, leaving the catheter, sheath, or cannula in place.

Complications are known to occur as a result of the Seldinger Technique. Regarding central venous catheters, such complications include arterial puncture, hematoma, air embolism, pneumothorax, infection, and traumatic nerve injury. Long-term complications include venous thrombosis, the formation of arteriovenous fistula, and pseudoaneurysms. Penetration of the posterior vessel wall during insertion has been thought to be a leading factor in ongoing mechanical central venous access complications. This may occur due to the speed and angle of needle insertion. Loss of needle access into the target lumen as a result of penetrating the posterior wall or other lapse in technique can ultimately result in trauma to the surrounding tissue or structures, especially if the operator continues with wire insertion and other procedural steps such as dilation, or has to repeat the procedure.

Central venous access complications are also attributed to other factors, including errors in sterile technique, the time taken to achieve access, and the number of needle passes through the skin and central vessels. Studies have suggested that the morbidity risk of central line procedures increases with the time needed to place the device, as well as the number of attempts to cannulate the vein. In addition, data suggest that the training and experience of the clinician may have an effect on patient complication rates.

The use of ultrasound guidance during placement of a catheter, sheath, or cannula is well-documented to reduce rates of complications in central venous catheter placement. The precise identification of vessel anatomy and visualization of the puncture site that is enabled through the use of ultrasound has contributed to lowering the morbidity of vascular access, making ultrasound guidance standard clinical practice. Ultrasound guidance also allows the clinician to visually locate the needle tip relative to patient anatomy in real time.

The ultrasound-guided modified Seldinger Technique is implemented in a manner largely similar to the Seldinger Technique in many respects. During the needle insertion step, the physician uses the syringe with a needle in one hand—typically the operator's dominant hand—and an ultrasound probe in the other hand in order to visualize the needle's trajectory and location inside the patient's body using alternating longitudinal and cross-sectional views with the ultrasound probe. Like with the Seldinger Technique, once the operator gains access to the targeted body space, which is confirmed when a specific body fluid is aspirated into the syringe's barrel, the operator holds the needle's hub with one hand and uncouples the syringe from the needle with the remaining hand. During this step, the ultrasound probe must be placed down resulting in loss of visualization of the needle in the targeted space. The removal of the ultrasound probe from the patient also releases the pressure of the probe on the tissue, resulting in a detrimental movement of tissue relative to the needle tip, thereby directly increasing risk of potential injury and losing access.

Because the ultrasound-guided modified Seldinger Technique (and the standard Seldinger Technique) requires the use of two hands to uncouple the needle from the syringe, stabilize the needle, and insert the guidewire into the targeted body space after the initial needle insertion step, there is a period of time during the procedure in which a sharp needle is located inside of a patient's body while the physician or other clinician cannot visualize it and has limited control over it. In particular, once the needle tip is inside the targeted body space the clinician must drop the ultrasound probe and perform hand switching motions that can uncontrollably move the needle. The clinician must also uncouple the syringe from the needle in a step that can also move the needle and reduce needle control. The clinician must also pass a guidewire through the needle's lumen in a process that can also move the needle relative to the targeted body space. The clinician must pass the guidewire without seeing the wire trajectory and location of the wire tip in real time. While ultrasound guidance helps with initial needle location and access, its advantages may be lost during the multiple steps requiring the use of both of an operator's hands. It may be used for verification after these steps, but at this point needle access may already be lost, with other structures entered and possibly traumatized. The wire could also be threaded into other, non-target tissues, such as the incorrect vessel, or could be kinked or become stuck in the patient. The process then must be repeated from the beginning leading to the additional time and needle punctures known to be associated with morbidity. Thus, despite the advantages of ultrasound guidance in its current form, adverse events continue to occur.

Although the Seldinger Technique is described here in the common setting of central venous access, it is important to recognize that the same principles apply to cannula insertion into other body spaces using the Seldinger Technique including the use of ultrasound. Other surrounding organs and structures may also be damaged secondary to needle and guidewire malposition. Abdominal procedures such as percutaneous nephrostomy and cholecystectomy, for example, may be complicated by bowel or vascular injury. The invention described herein may similarly be applied in other settings where the Seldinger Technique is used, especially but not exclusively with ultrasound. Needle, wire, and catheter sizes used during these procedures may vary for different target organs and objectives; however, the invention may be adapted using industry standard interlocking systems for different components or by specific design parameters applied to the inventions disclosed herein. It will be understood that each of the inventions disclosed herein, even where described in the context of central venous access, are equally and directly applicable to other body access procedures included, but not limited to, arterial line placements, angiograms, percutaneous tracheostomies, pleural catheter placement, percutaneous cholecystectomy, percutaneous nephrostomy, and percutaneous abscess drainage.

Description of the Related Art

A number of access devices are known. For example, U.S. Pat. No. 8,915,884 discloses an access device that places a medical article within a body space of a patient. The device has a needle section that includes an elongated body and a needle hub. The device further includes a dilator portion that has a dilator and a dilator hub. The dilator is coaxially disposed and slideable over the elongated body of the needle section. The sheath is coaxially disposed and slideable over the dilator. The device further includes a first locking mechanism operably disposed between the needle hub and the dilator hub to inhibit at least unintentional axial movement between the needle section and the dilator portion and a second locking mechanism operably disposed between the dilator hub and the sheath hub to inhibit at least unintentional axial movement between the dilator portion and the sheath section.

As another example, U.S. Patent Application Publication No. 2015/0224267 discloses a safety needle system operable with a medical device includes: a housing with a needle mount having a needle; and a sheath telescopically engaged with the housing and surrounding the needle such that the sheath operates in a retracted position, in which the sheath exposes the needle, and an extended position, in which the sheath surrounds the needle. The sheath is coupleable to the medical device such that removal of the needle from the medical device draws the sheath over the needle, transitioning the sheath from the retracted position to the extended position. In one embodiment, the system includes a slider engaged with the sheath and/or housing and including a restraint that engages and disengages the sheath to respectively reinforce and weaken the coupling of the sheath and medical device. In another embodiment, the sheath includes a longitudinal track that slidingly engages a setting of the housing between sheath positions.

However, the operation of these inventions particularly for guidewire insertion requires the use of two hands. Where two hands are required for operation of procedures, any ultrasound visualization will necessarily be lost during the procedure. Therefore, it is apparent for the above that there is an ongoing need for new instruments, particularly instruments designed for single-handed operation for the placement of articles, such as guidewires, into veins, arteries, vessels, body cavities, and drainage sites of patients during access procedures.

The inventions disclosed and taught herein are directed to an improved apparatus and method for accessing a space in a body and inserting an article into that space. More particularly, the inventions disclosed herein allow for single-handed access into a body space, confirmation of access such as through application of suction, and securing access such as by guidewire insertion. This single-handed operation feature allows the operator to retain ultrasound visibility and stability while the guidewire is inserted, which, in turn, allows the operator to verify that the guidewire is going into the correct body space and that the needle does not move out of the targeted body space after achieving initial needle insertion. The apparatus may optionally also incorporate a protective sheath that can be used to shield the patient's anatomical structures from the needle tip immediately after initial needle insertion is obtained. Moreover, when the apparatus is equipped with a sheath, the sheath partially secures access and facilitates guidewire insertion.

BRIEF SUMMARY OF THE INVENTION

Briefly summarized, embodiments of the present invention are directed to an insertion apparatus for insertion of an article into a body. More particularly, the embodiments of the insertion apparatus of the present invention are directed to inserting a guidewire or similar article into a targeted body space of a patient. Such a targeted body space may commonly be a vein and the article for inserting into the targeted body space a guidewire. The insertion apparatus combines needle insertion, suction application through the needle, guidewire insertion and pressure monitoring into a single device that is operable using a single hand. The insertion apparatus may optionally also include a sheath movably attached to the housing and configured to be able to be selectively advanced to cover the distal end of the needle. The sheath may be detachable from the housing and the needle removed from it to maintain a port into the targeted body space.

In some various embodiments of the invention, the insertion device comprises a housing, a piercing structure with a lumen, wherein the piercing structure extends distally from the housing, a vacuum chamber that communicates with the lumen of the piercing structure, a guidewire, and a pressure-monitoring channel, wherein the insertion device is configured to be operated with a single hand. The insertion device is configured to permit the piercing structure to be inserted into the body, while suction is applied through the lumen of the needle. When the targeted body space has been reached, the insertion device is configured such that the guidewire can be advanced into the targeted body space using the single hand of the user and a pressure representative of the body part may be continuously communicated to the insertion device.

In use, the housing of the insertion device is gripped with a single hand of the user. The distal end of the piercing structure is inserted into the patient. Simultaneously, the user applies suction using a suction apparatus to confirm the targeted body space of the patient has been accessed. For instance, confirmation of piercing structure access to the lumen of a vein of the patient would be confirmed by the return of venous blood through the piercing structure lumen and/or visual ultrasound confirmation of needle tip location. Once placement of the piercing structure in the targeted body space is confirmed, the user advances the guidewire into the targeted body space using the single hand and can watch the wire trajectory in real time via ultrasound. At any point in the procedure, the pressure in a pressure-monitoring channel may be transduced to determine, for example and without limitation, an pressure waveform at a discrete time, or a continuous pressure waveform.

In some embodiments of the insertion apparatus, the housing includes grips configured to accommodate at least one finger of the user. In some embodiments of the insertion apparatus, a sheath is coaxially disposed about the piercing structure and is affixed to a sheath movement element that is movably affixed to the housing. The sheath can itself be removably or permanently affixed to the sheath movement element. In some embodiments, the vacuum chamber can be separate from the housing, or alternatively can be integrated with the housing. These and other features of embodiments of the present invention will become more fully apparent from the following description and appended claims, or may be learned by the practice of embodiments of the invention as set forth herein.

DETAILED DESCRIPTION OF THE INVENTION

Figure 1:
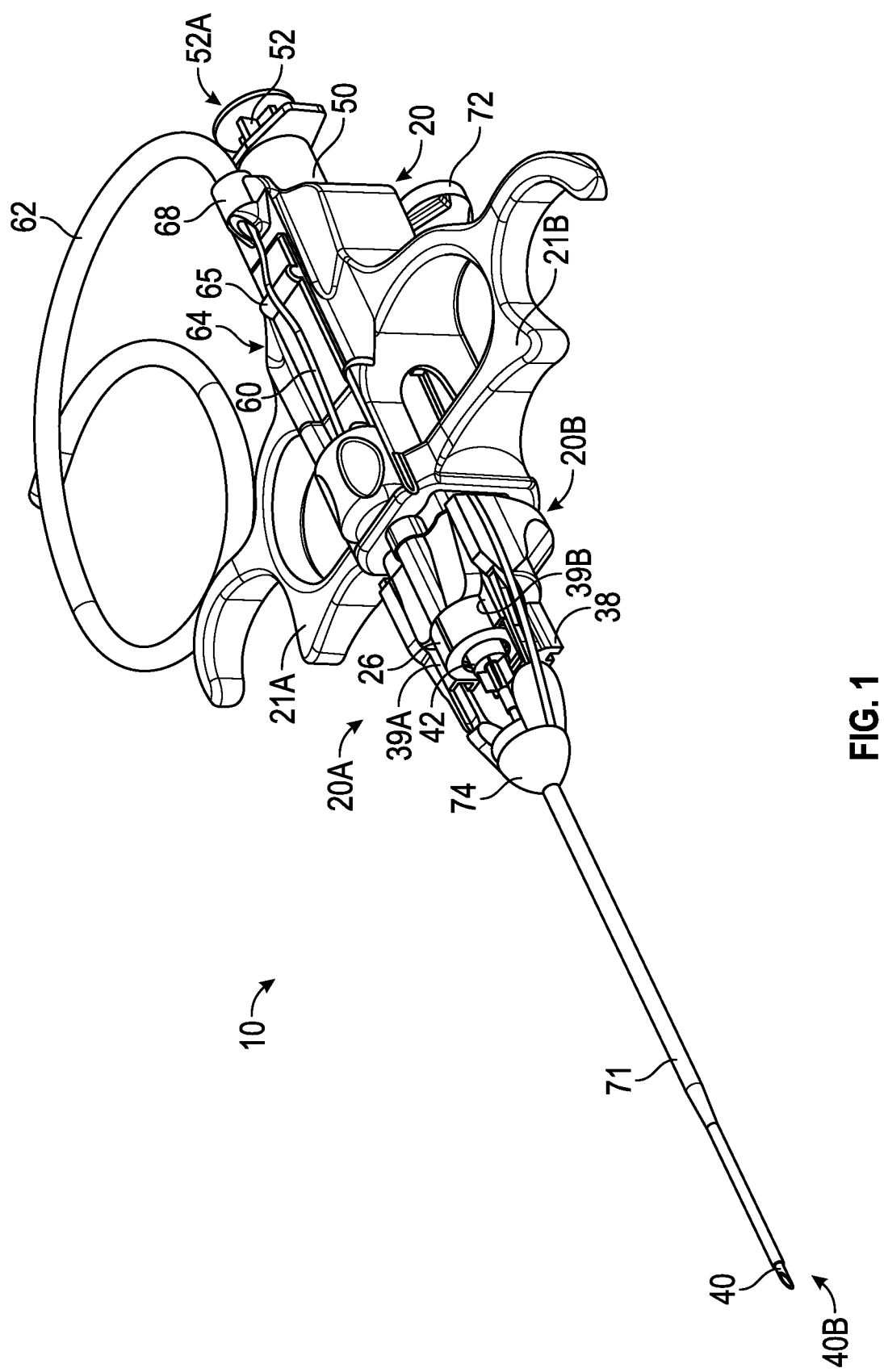
FIG. 1 illustrates a top perspective view of the insertion device in accordance with one embodiment.
Figure 2:
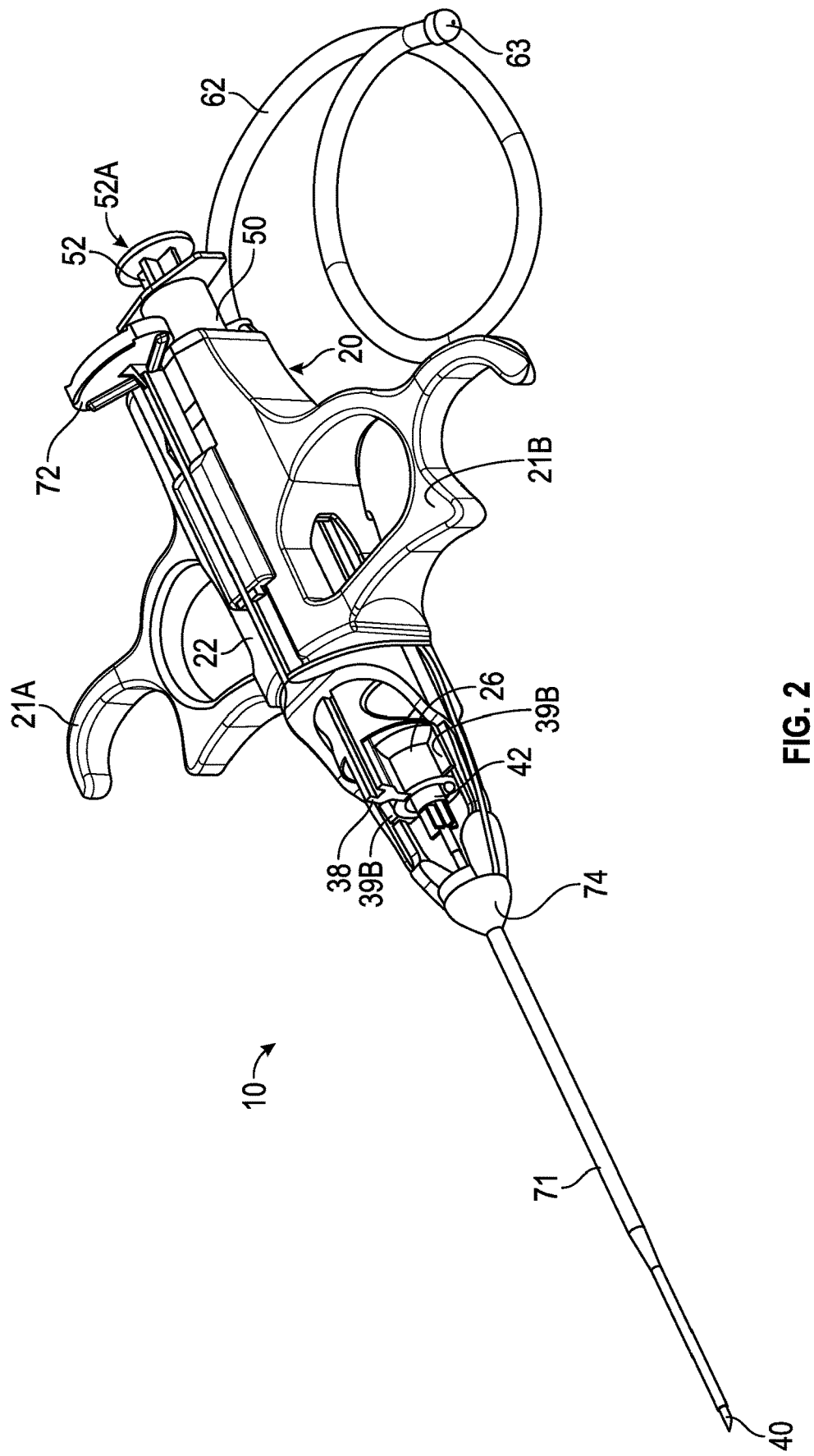
FIG. 2 illustrates a bottom perspective view of the insertion device in accordance with the embodiment depicted in FIG. 1.
Figure 3:
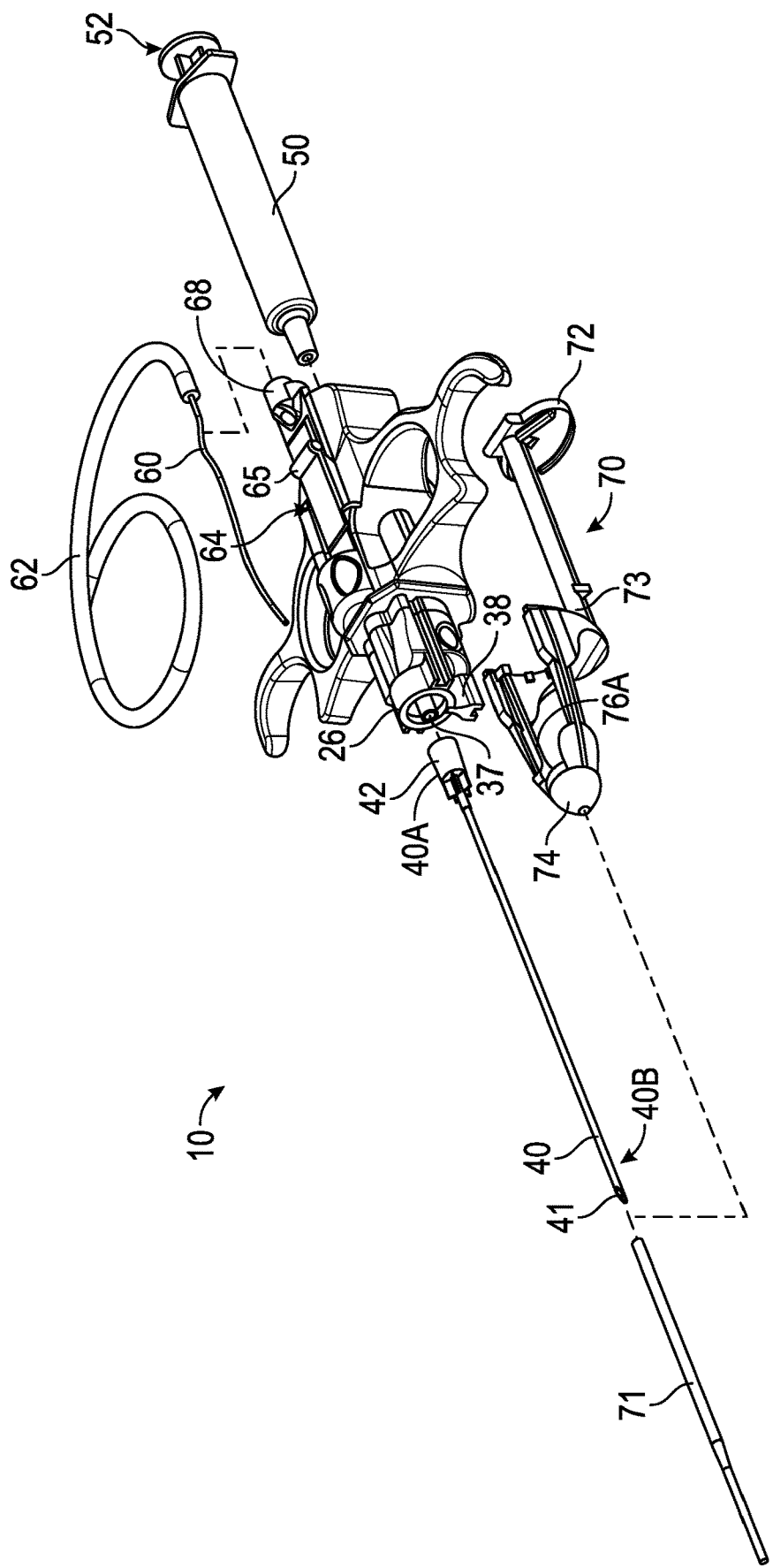
FIG. 3 illustrates a top perspective exploded view of the insertion device in accordance with the embodiment depicted in FIG. 1.
Figure 4:
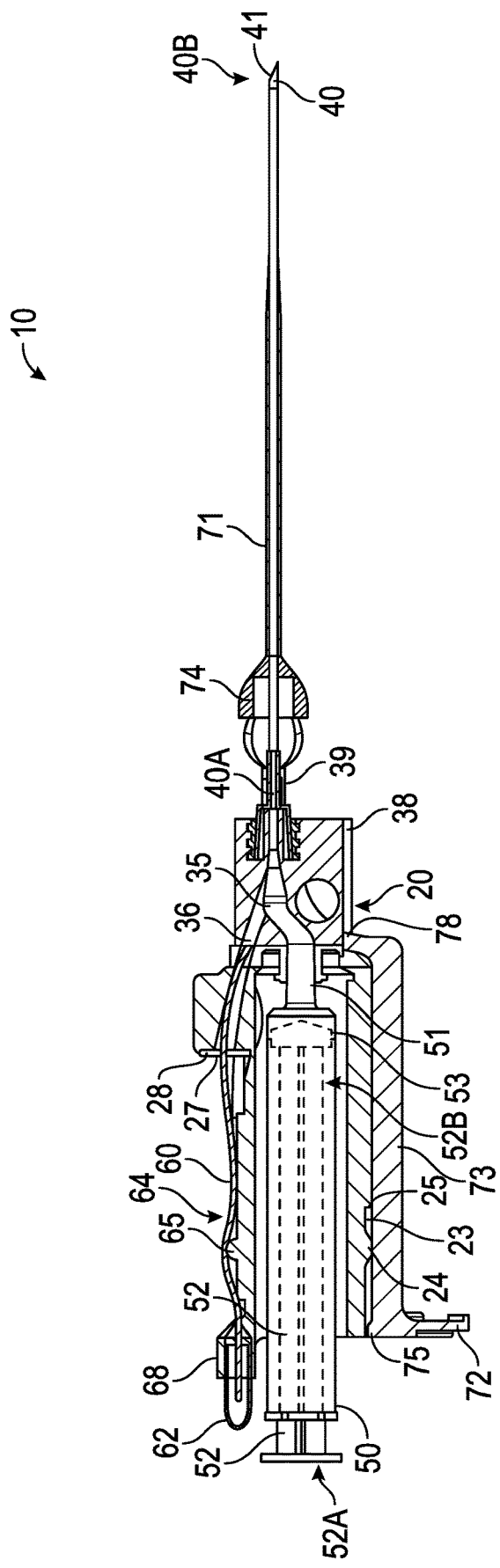
FIG. 4 illustrates a side cross-sectional view of the insertion device in accordance with the embodiment depicted in FIG. 1.

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. For clarity, it is to be understood that the word "proximal" refers to a direction relatively closer to a clinician using the device to be described herein, while the word "distal" refers to a direction relatively further from the clinician. For example, the end of a needle placed within the body of a patient is considered a distal end of the needle while the needle end remaining outside the body is a proximal end of the needle. Also, the words "includes," "including," "has," and "having" as used herein, including the claims, shall have the same meaning as the word "comprising." Also, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Applicants have created an insertion device for inserting a guidewire or similar article into a targeted body space of a patient using a single hand. The targeted body space may commonly be a vein and the article for inserting into the targeted body space a guidewire. The insertion device combines needle insertion, suction application through the needle, and guidewire insertion into a single device that is operable using a single hand. The insertion device may optionally also include a sheath movably attached to the housing and configured to be able to be selectively advanced to cover the distal end of the needle. The sheath may be detachable from the housing to maintain a port into the targeted body space.

In some various embodiments of the invention, the insertion device comprises a housing, a piercing structure with a lumen, wherein the piercing structure extends distally from the housing, a vacuum chamber that communicates with the lumen of the piercing structure, and a guidewire, wherein the insertion device is configured to be operated with a single hand. The insertion device is configured to permit the piercing structure to be inserted into the body, while suction is applied through the lumen of the needle. When the targeted body space has been reached, the insertion device is configured such that the guidewire can be advanced into the targeted body space using the single hand of the user.

In use, the housing of the insertion device is gripped with a single hand of the user. The distal end of the piercing structure is inserted into the patient. Simultaneously, the user applies suction using a suction apparatus to confirm the targeted body space of the patient has been accessed. For instance, confirmation of piercing structure access to the lumen of a vein of the patient would be confirmed by the return of venous blood through the piercing structure lumen and/or visual ultrasound confirmation of needle tip location. Once placement of the piercing structure in the targeted body space is confirmed, the user advances the guidewire into the targeted body space using the single hand and can watch the wire trajectory in real time via ultrasound.

In some embodiments of the insertion apparatus, the housing includes grips configured to accommodate at least two fingers of the user. In some embodiments of the insertion apparatus, a sheath is coaxially disposed about the piercing structure and is affixed to a sheath movement element is movably affixed to the housing. The sheath can itself be permanently or removably affixed to the sheath movement element. In some embodiments, the vacuum chamber can be separate from the housing, or alternatively can be integral with the housing.

FIGS. 1-4 depict various details of the insertion apparatus ("insertion apparatus," "insertion tool," or "insertion device"), generally depicted at 10, according to one embodiment. As shown, the insertion device includes a main housing 20. Main housing 20, for reference in the figures, has a top side 20A and a bottom side 20B. Main housing 20 may include handles, 21A and 21B, as depicted in this particular embodiment. Handles 21A and 21B are configured to facilitate a user gripping and operating the insertion device using one hand and aspirating body fluid, as will be described in further detail below. In this embodiment, handles 21A and 21B comprise both a full-loop and a half-loop finger grip on each side of main housing 20. In alternative embodiments, the handles may comprise only half-loop or only full-loop finger grips, and may number one to four on either side or both sides of main housing 20. In the present embodiment, main housing 20 is composed of a thermoplastic such as polycarbonate and is substantially transparent, although manufacture using other suitable materials will readily be apparent to a person of skill in the art. If main housing 20 is made using a substantially non-transparent material, such as a substantially translucent or substantially opaque thermoplastic, it may be desirable to include cut-out or window areas in housing 20 to permit a user to visualize needle hub 42 or vacuum chamber 50 during use as will be explained more fully below.

A hollow piercing structure, such as needle 40, is affixed to a needle hub 42 at the proximal end 40A of needle 40. The proximal end 40A of the needle 40 fits into a pocket in needle hub 37 and is fixed in place using an appropriate adhesive or other appropriate means as would be appreciated by a person of skill in the art. Needle 40 extends distally from needle hub 37 to distal end 40B of the needle 40 where it terminates at a point or other sharp end suitable for piercing skin of a patient, such as bevel 41. Needle hub 37 is configured to fit on the needle hub attachment 26 at the distal end of main housing 20. The needle hub attachment 26 may or may not taper from the proximal end to the distal end, depending on the configuration of needle hub 37. In this embodiment, needle hub attachment 26 is a male Luer-Lok connection fitting; needle hub 37 is a corresponding female Luer-Lok fitting. However, it will be understood that other appropriate fittings may be used, including friction fittings, to create a connection between needle hub 37 and needle hub attachment 26. Appropriate fittings or other means of attaching the needle to the housing will create a connection that is substantially air-tight, as will be explained below. In some embodiments of the inventions, it may be desirable to provide an adjustable or removable connection between needle 40 and main housing 20 to permit the user to rotate needle 40 to adjust the orientation of needle bevel 41 relate to main housing 20. It will also be appreciated that alternative embodiments of the inventions described herein need not require that needle 40 is removable, with a needle hub 37 or otherwise; indeed, alternative embodiments of the inventions described herein may include a needle 40 that is permanently attached to or otherwise an integral part of main housing 20. Whether needle 40 is bonded to needle hub 37 or directly to main housing 20, it is envisioned that a bond strength of at least about 3 in-lbs would be adequate for the practice of the inventions disclosed herein, recognizing that lower or higher needle bond strengths may be sufficient or even preferable depending on the specific application to which the embodiments of the inventions are used.

Insertion device 10 further includes a means to create a vacuum to provide a suction. Specifically, suction would be provided as a pressure differential between the distal end 40B of needle 40 and the suction means. In the present embodiment, the suction means is provided as a vacuum chamber 50 and a plunger 52. As depicted in FIGS. 1-4, vacuum chamber 50 is shown as the barrel of a syringe. However, it will be apparent from this disclosure that vacuum chamber 50 need not be a syringe barrel that can be separated from main housing 20 as depicted in this embodiment. Alternatively, vacuum chamber 50 can be a portion of and contiguous with main housing 20. In each embodiment, the volume of vacuum chamber 40 preferably is sufficient to provide for the aspiration of a volume of at least 4 milliliters of fluid, although a smaller volume could also be acceptable to practice the inventions disclosed herein. The distal end 52B of plunger 52 includes a head 53 that creates a substantially air-tight annular seal against the wall of vacuum chamber 50. In this embodiment, vacuum chamber 50 is depicted with nozzle 51 that fits substantially securely, by use of a friction fitting, into main housing 20 as shown. Alternative fittings, such as a male Luer-Lok fitting on the nozzle of vacuum chamber 50 and a female Luer-Lok fitting in main housing 20 would also be appropriate in this embodiment of insertion device 10. The fitting of nozzle 51 to housing 20 makes a substantially air-tight seal between vacuum chamber 50 and lumen 35 in main housing 20. Upon attachment of vacuum chamber 50 to main housing 20, vacuum chamber 50 communicates with lumen 35, which, in turn, communicates with the lumen of needle 40 from the distal opening 37 in housing 20 such that fluid can flow from distal end 40B of needle 40, through the needle lumen, through lumen 35, through nozzle 51, and into vacuum chamber 50. In other words, lumen 35 serves as a conduit between the lumen of needle 40 and vacuum chamber 50. The proximal plunger end 52A can optionally be configured to include a grip (not shown in FIGS. 1-4) such as a full or partial ring. The addition of a grip can be used by a clinician when drawing back plunger 52 with his or her thumb to create a vacuum in vacuum chamber 50.

Insertion device 10 further includes a guidewire 60. It is contemplated that insertion device 10 should be compatible with at least a 0.038-inch sized guidewire, although a person of skill in the art will appreciate that insertion device 10 may be designed to be specifically compatible with alternatively sized guidewires as may be necessary for a variety of procedures, practices, and applications. In this embodiment, guidewire 60 is disposed within guidewire housing 62, and guidewire housing 62 is removably attached to main housing 20 at connector 68. Guidewire housing 62 may be rigid or flexible, and is generally of sufficient length to hold the length of guidewire 50. Further, guidewire housing 62 can be either removably or permanently attached to main housing 20, or could be an integral part of main housing 20. Guidewire housing 62 may additionally include a cap 63. If present, cap 63 could serve a variety of purposes, including isolating guidewire 60 from the surrounding environment or to prevent guidewire 60 from being pushed out the proximal end of guidewire housing 62. Main housing 20 is configured to allow the movement of guidewire 60 from the distal end of guidewire housing 62 at or about connector 68 along guidewire feed region 64 into lumen 36 of main housing 20. Lumen 36 connects with lumen 35 in the main housing 20 at a point proximal to the connection of needle hub 37 to needle hub attachment 26. Lumen 36 is configured to receive guidewire 60 at opening 27. Lumen 36 is further configured to be fitted with a valve 28 between opening 27 and the point where lumen 36 joins with lumen 35. Valve 28 is configured to allow the passage of guidewire 50 but to prevent the substantial flow of air that would substantially defeat a vacuum created by the proximal movement of plunger 52 in vacuum chamber 50. It will be recognized by a person of skill in the art that while in this embodiment valve 28 is located at opening 27, valve 28 could be placed at any location along lumen 36. Moreover, it will be recognized by a person of skill in the art that a valve may not be necessary if guidewire 60 fits within lumen 36 tightly enough to prevent the substantial flow of air through lumen 36 such that the creation of a vacuum in vacuum chamber 50 is defeated. Furthermore, any variety or types of valves or other methods to maintain the pressure differential could be employed, as will be appreciated by a person of sill in the art. Such a valve or method could, for example, be pressure-sensitive. For purposes of the inventions described herein, the seal between guidewire 60 and the wall of lumen 36, whether or not valve 28 is employed, should be able to maintain a pressure differential of at least about 300 mmHg, although the inventions described herein could be practiced if a pressure differential of less than 300 mmHg was maintained across lumen 36.

In this embodiment, guidewire feed region 64 includes protrusion 65 between guidewire housing connector 68 and opening 27 to lumen 36, over which guidewire 60 passes. Guidewire feed region 64 is generally configured to be accessible by the thumb of the user while gripping main housing 20 with one hand; however, the configuration may be altered in some embodiments of the present inventions such that the guidewire feed region 64 is accessible by a finger of the one hand of the user gripping main housing 20. In this embodiment, the thumb of the user can be used to advance guidewire 50 through needle 40 toward distal end 40B of needle 40 and into the targeted body space of the patient. Of course, the thumb of the user may also be used to move guidewire 50 in the opposite direction, toward proximal end 40A of needle 40, for instance if guidewire 50 needs to be retracted into the lumen of needle 40 and repositioned, or otherwise retracted from the targeted body space. Protrusion 65 can serve to provide tactile feedback to the clinician while advancing (or retracting) guidewire 60, as well as to provide a raised surface to press against while advancing guidewire 60 to assist in the gripping of guidewire 60 to increase the efficiency of movement of guidewire 60. It will be appreciated that protrusion 65 can be replaced with other suitable structures configured to assist a user in moving guidewire 60 along the guidewire feed region 64 in either a proximal or distal direction. Such suitable structures may include a pin and wheel arrangement, raised plate, partial sphere, or the like. Protrusion 65 may be aligned with an initial length marker on guidewire 60, and compared to sequential markers on guidewire 60 to indicate the length of guidewire 60 that has been inserted into the patient.

In this embodiment, insertion device 10 includes a sheath 71 that is coaxially moveably disposed about needle 40. Sheath 71 could optionally be echogenic to promote visualization via ultrasound. Sheath 71 is attached to sheath movement element 70 at sheath hub 74. Sheath 71 may be permanently affixed to sheath movement element 70 at sheath hub 74 or may be removably attached, depending on the application and the specific use of the embodiment. Where sheath 71 is removably attached, sheath attachment would be configured so that sheath can be left in the tissue of the patient to provide a port through which the targeted tissue can be accessed. In this embodiment, sheath movement element 70 includes pusher 72, spanning element 73, sheath hub 74, tab 75, and groove connector 76. Pusher 72 is configured to permit a user, while gripping main housing 20 with a single hand, to move sheath movement element 70 in proximal and distal directions using the thumb of the single hand. Movement of sheath movement element 70 in a distal direction would result in sheath 71 moving coaxially along needle 40 toward the needle distal end 40B. Further, both the length of sheath 71 and the degree of movement permitted of sheath movement element 70 is sufficient to permit the furthest movement of sheath 71 in a distal direction to cover distal end 40B of needle 40 to shield distal end 40B of needle 40. Conversely, movement of sheath movement element 70 in a distal direction would result in sheath 71 moving coaxially along needle 40 away from distal end 40B of needle 40. Continued movement of sheath movement element 70 would result in the exposure of needle distal end 40B. Movement of the sheath movement element 70 in a distal direction from the position depicted in FIG. 4 results in tab 75 of sheath movement element 70 passing over ridge 24 and resting in notch 23 of housing 20. Notch 23 is created on the proximal end by ridge 24 and on the distal end by stopper 25. The contact of tab 75 with stopper 25 arrests the distal advancement of sheath movement element 70, and therefore the extent of movement of sheath 71 in the distal direction. In use, the passage of tab 75 over ridge 24 creates tactile feedback to inform the clinician that the furthest extent of sheath 60 advancement is being reached. In addition, when tab 75 is resting in notch 23, proximal movement of sheath movement element 70 is partially restricted by ridge 24, thereby reducing the possibility of accidental retraction of sheath 71. Sheath movement element 70 is moveably attached to housing 20 by the joining of groove 78 of sheath movement element 70 to rail 38 of main housing 20 and by joining grooves 39A and 39B on the right and left sides of main housing 20, respectively, to rails 76A and 76B, respectively, of sheath movement element 70. Sheath movement element 70 may be configured to be removable from main housing 20 by a user if the sheath functionality is not desired for a particular application of the inventions.

In this embodiment of insertion device 10, sheath movement tab 72 is disposed on the bottom 21B of housing 20 and guidewire 50 is disposed on the top 21A of housing 20. However, it will be appreciated by persons of skill in the art that the inventions described herein can be practiced with both the sheath movement tab 72 and the guidewire 50 disposed on the same side of housing 20. Examples of such embodiments are described in detail below.

Figure 5:
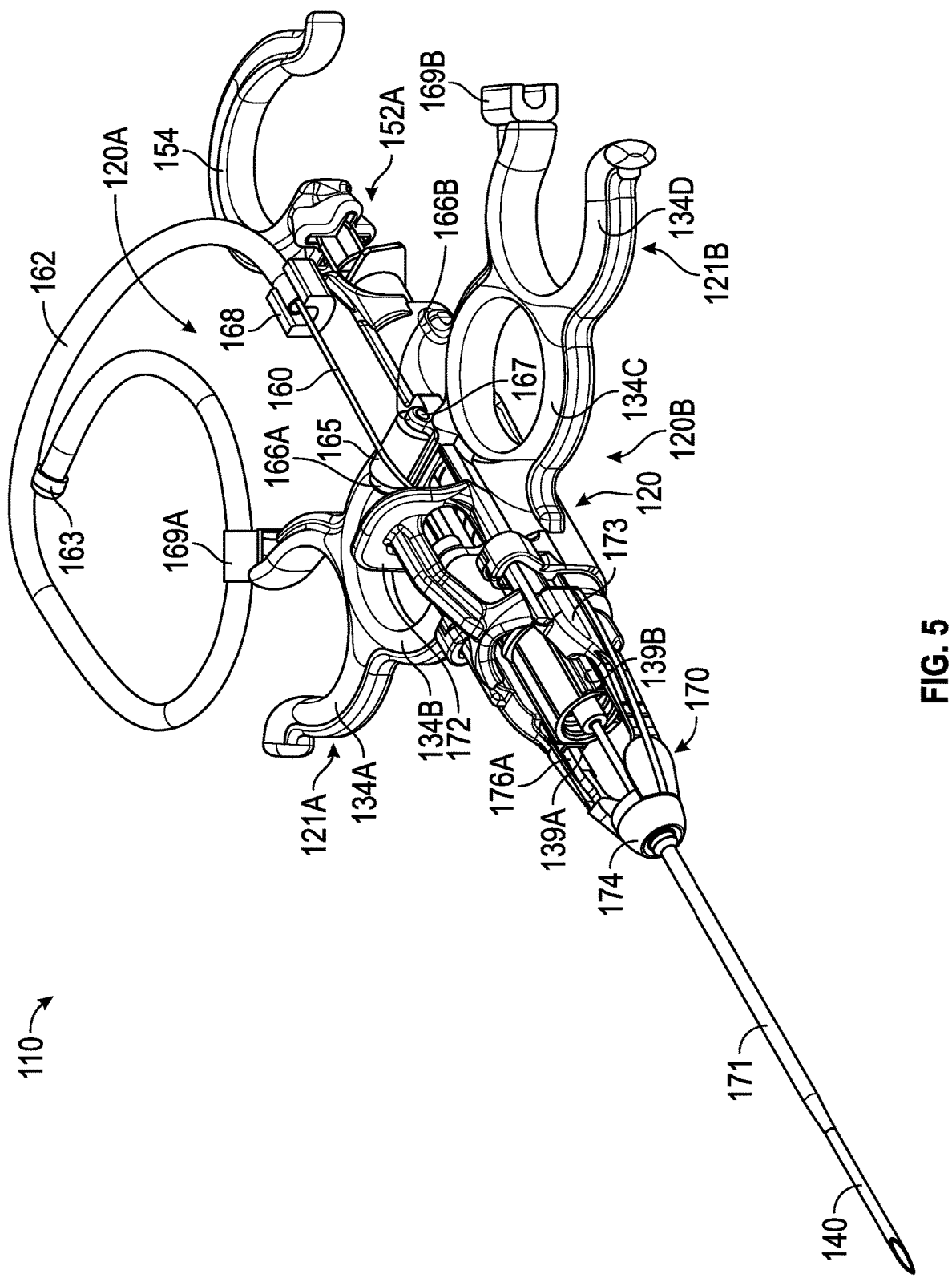
FIG. 5 illustrates a top perspective view of the insertion device in accordance with another embodiment.
Figure 6:
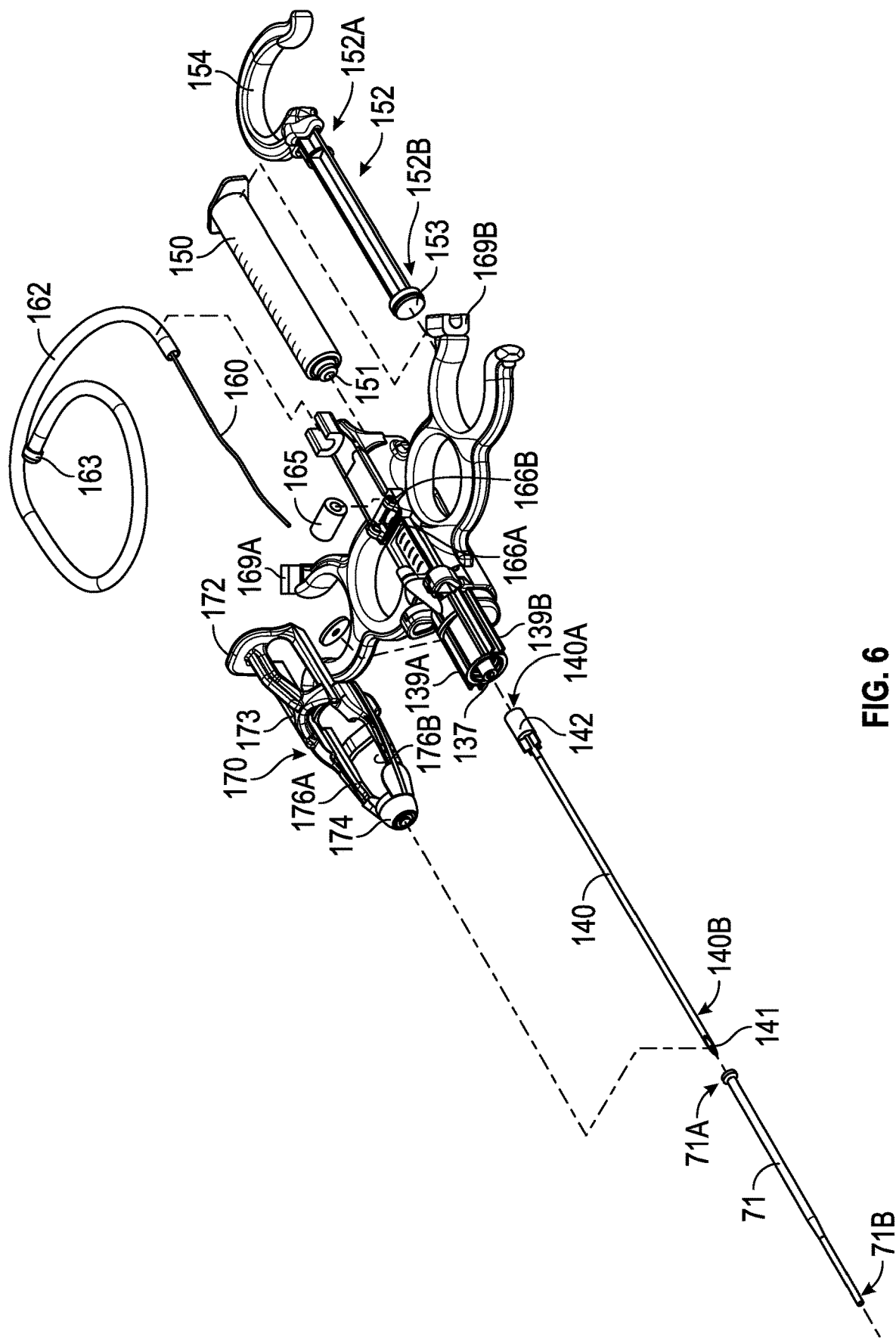
FIG. 6 illustrates a top perspective exploded view of the insertion device in accordance with the embodiment depicted in FIG. 5.
Figure 7:
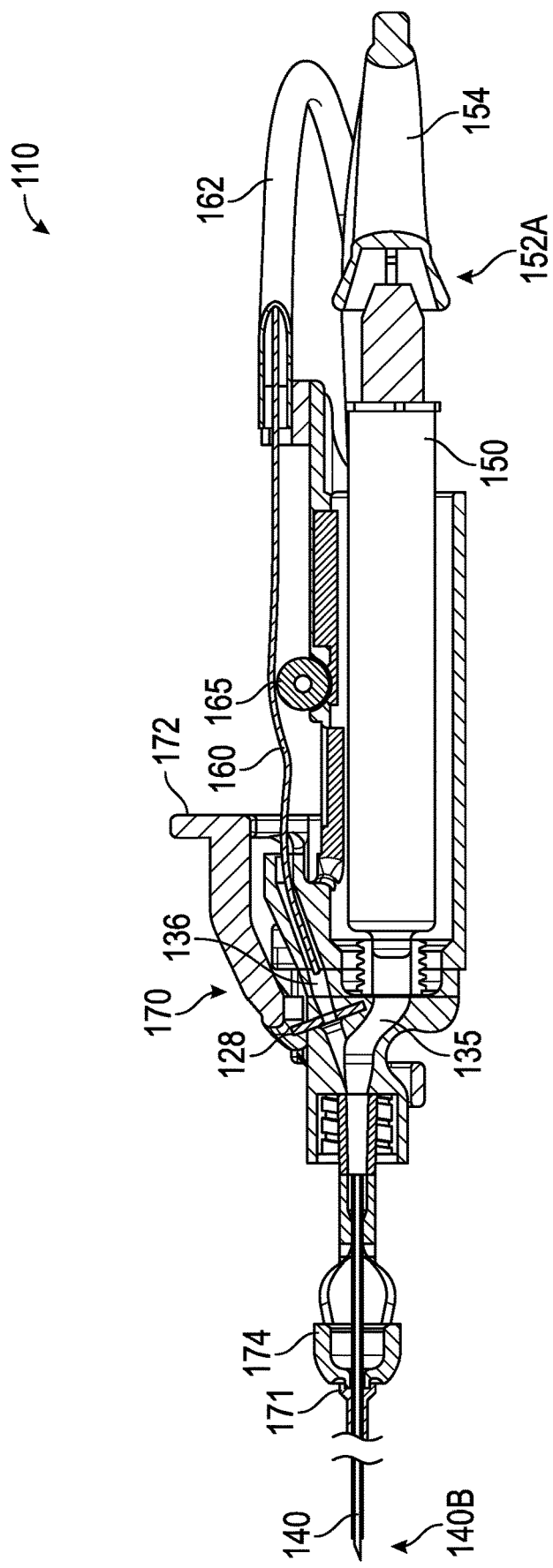
FIG. 7 illustrates a side cross-sectional view of the insertion device in accordance with the embodiment depicted in FIG. 5.

For example, FIGS. 5-7 depict an embodiment of the inventions described herein where the movement of a sheath and the movement of the guidewire are controlled by the user from the same side of the insertion device. One of the advantages of the inventions described herein, as previously explained, is to permit a clinician, or user, to insert a guidewire to secure access to a body space such as a vein using one hand. With the inventions disclosed herein, a clinician is able to puncture the body of a patient with a needle, confirm access to a targeted body space by aspirating fluid through that needle, and advance a guidewire to secure access into the targeted body space using a single hand. As explained herein, the ability to perform all of these activities with a single hand has numerous benefits for the clinician as well as the patient. To optimize the performance of all of these activities—piercing, confirming access, and securing access with a guidewire—the inventions described herein should allow the clinician to maintain hand position and function in an ergonomically beneficial manner. The consideration of human factors and ergonomics in the specific design and layout of the inventions described herein should allow for the insertion device to be maintained in an ergonomically-beneficial position such that the clinician is capable of puncturing the patient and advancing the needle of the invention device while aspirating fluid through the needle into the vacuum chamber of the insertion device. It will be apparent to a person of skill in the art that an additional ergonomic consideration is to permit the clinician to maintain fine control of the needle tip while aspirating fluid during insertion. It is also desirable that the clinician can clearly visualize the aspirated fluid while inserting the needle and simultaneous aspirating body fluid through the advancing or advanced needle.

While not necessary for the practice of the inventions described herein, it may be beneficial for the use of the insertion device that the guidewire be staged, or pre-loaded, in the needle during insertion of the needle into the patient so that the guidewire can be advanced into the targeted body space quickly after access to the targeted body space has been confirmed. Alternatively, it may be beneficial to pre-load the guidewire into the housing conduit distal to the valve but proximal to the needle lumen. It may be beneficial in some embodiments of the inventions disclosed herein that the insertion device has the ability to store some length of guidewire that may be required during the access procedure. It may further be beneficial that the guidewire storage location be protected from the environment to keep the guidewire clean and/or sterile and to prevent the length of guidewire from interfering with the access procedure.

Returning now to FIGS. 5-7, an embodiment of insertion device 110 according to the present inventions is depicted. As shown, the insertion device includes a main housing 120, which has a top side 120A and a bottom side 120B when oriented during use by a clinician and for reference in these figures. As depicted, main housing 120 may include handles 121, where, as referred to in the figures, the right handle 121A and the left handle 121B are depicted from the perspective of a clinician, when insertion device 110 is oriented as it would be during use by the clinician. Handles 121A and 121B are configured to ergonomically facilitate the user gripping insertion device 110 by holding main housing 120 using a single hand as well as to facilitate aspiration, as will be further described below. Each handle 121A and 121B comprise a full-ring finger grip (134B, 134C) closer to main housing 120 and an open-ring finger grip (134A, 134D) further from main housing 120. However, it will be recognized that any combination of full-ring and open-ring finger grips may be utilized in the present invention, as well as varying numbers of finger grips on either side of main housing 120 can be employed when practicing the inventions described herein. In this embodiment, handles 121A and 121B are provided symmetrically on the right and left side of main housing 120 to permit use by both right-hand dominant and left-hand dominant clinicians, as well as to allow for a variety of finger orientations as may be preferred by various individual clinicians. For example, in one method of gripping insertion device 110, a right-hand dominant user would hold insertion device 110 in the right hand with the top 120A of main housing 120 pointing upwards, and the palm of the user's hand oriented against the bottom 120B of main housing 120. The orientation and position of fingers can vary according to the preference and comfort of the clinician. For instance, a user may choose to orient his or her grip so that the tip of the first, or index, finger is inserted in the full ring grip of the right handle 121A. The second finger may be inserted in the full ring closest to main housing 110 of left handle 121B. The third finger could then be positioned in the open ring of handle 121B, further from main housing 110. It should be noted that the reference to "top" and "bottom" and "right" and "left" is used only for purposes of describing the possible gripping and ergonomic disposition of insertion device 110, and is not meant in any way to suggest that the "top" and "bottom" and "right" and "left" orientation is to be maintained during use of the insertion device 110. For instance, a user may find the most comfortable and effective orientation of insertion device 110 is to hold insertion device 110 with what is referred to here as the right handle 121A oriented up, allowing the clinician to have the fifth finger of the hand nearest to the patient, using the small finger to brace the hand against the patient and help stabilize insertion device 110 and allow for even greater control of needle 140 movement during insertion and aspiration. With insertion device 110 being grasped by the fingers of the dominant hand, for example as described above, the clinician's thumb is free to manipulate, for example, plunger 152 by use of grip 154, guidewire 160, and sheath movement tab 172. Additional details of use of embodiments of this invention are described below.

Main housing 120 is composed of thermoplastic such as polycarbonate and is substantially transparent, although as with other embodiments of the present inventions, manufacture of main housing 120 may be performed using other suitable materials will readily be apparent to a person of skill in the art. If main housing 120 is made using a substantially non-transparent material, such as a substantially translucent or substantially opaque thermoplastic, it may be desirable to include cut-out or window areas in main housing 120 to permit a user to visualize needle hub 142 or vacuum chamber 150 during use. Main housing 120 is illustrated herein as comprising a single, unitary piece, manufactured using a suitable method such as injection molding or 3D printing. However, it will be appreciated that main housing 120 could be constructed using multiple pieces, such as a top and a bottom in a shell-like arrangement, as long as the bonding of such top and bottom pieces was sufficiently air-tight to allow an appropriate vacuum to be maintain in vacuum chamber 150 and lumens 135 and 136. In the present embodiment, however, maintenance of the seal in vacuum chamber 150 would not be dependent on a seal between a top portion and a bottom portion of housing 120 because in this embodiment vacuum chamber 150 comprises a unitary syringe barrel.

A hollow piercing structure, such as needle 140, is affixed to a needle hub 142 at the proximal end 140A of needle 140. The proximal end 140A of the needle 140 fits into a pocket in needle hub 137 and is fixed in place using an appropriate adhesive or other appropriate means as would be appreciated by a person of skill in the art, including, for instance, but not limited to, ultra-violet cured epoxy. Needle 140 extends distally from needle hub 137 to distal end 140B of the needle 140 where it terminates at a point or other sharp end suitable for piercing skin of a patient, such as bevel 141. Needle hub 137 is configured to fit on the needle hub attachment 126 at the distal end of main housing 120. Needle hub attachment 126 may or may not taper from the proximal end to the distal end, depending on the configuration of needle hub 137. In this embodiment, like other embodiments that include a needle hub, needle hub attachment 126 is a male Luer-Lok connection fitting and needle hub 137 is a corresponding female Luer-Lok fitting. A person of skill in the art will appreciate that other appropriate fittings may be used, including friction fittings, to create a connection between needle hub 137 and needle hub attachment 126. Appropriate fittings or other means of attaching the needle to the housing will create a connection that is substantially air-tight, as will be explained below, and will allow for a pressure differential to be maintained between the distal end 140B of needle 140 and vacuum chamber 150 of at least about 300 mmHg. In some embodiments of the inventions, it may be desirable to provide an adjustable or removable connection between needle 140 and main housing 120 that permit the user to rotate the orientation of needle 140 to adjust the direction of angle of needle bevel 141 relate to main housing 120. Such adjustment of needle bevel 141 may be useful to accommodate ambidextrous usage of insertion device 110 and to accommodate clinician personal preferences. It will also be appreciated that alternative embodiments of the inventions described herein need not require that needle 140 is removable. It will be appreciated that where needle 140 is not removable, needle 140 may be permanently attached to or otherwise integral with main housing 120. Whether needle 140 is bonded to needle hub 137 or directly to main housing 120, it is envisioned that a bond strength of at least about 3 in-lbs would be adequate for the practice of the inventions disclosed herein, recognizing that lower or higher needle bond strengths may be sufficient or even preferable depending on the specific application to which the embodiments of the inventions are used.

Vacuum chamber 150 is included in insertion device 110, allowing for the creation of a suction sufficient to aspirate fluid from the distal end 140B of needle 140, through the lumen of needle 140, and into vacuum chamber 150. As previously explained, it is believed that a suction of at least approximately 300 mmHg should be sufficient for the practice of the inventions described herein, although it will be apparent that lower pressure differentials may be sufficient, depending on the specific design of the embodiment and the specific application in which it will be used. As depicted in FIGS. 5-7, vacuum chamber 150 is depicted as the barrel of a syringe. However, and as described previously, it will be apparent from this disclosure that vacuum chamber 150 need not be a separate syringe barrel. Alternatively, vacuum chamber 150 can be a portion of and contiguous with main housing 120. The volume of vacuum chamber 150 preferably is sufficient to provide for the aspiration of a volume of at least 4 milliliters of fluid, although a smaller volume could also be acceptable to practice the inventions disclosed herein. Distal end 152B of plunger 152 includes a head 153 that is capable of creating a substantially air-tight annular seal against the wall of vacuum chamber 150. In this embodiment, vacuum chamber 150 is depicted with nozzle 151 that fits substantially securely, by use of a male Luer-Lok fitting, into a female Luer-Lok fitting that is included in main housing 120 as shown in FIG. 7. In this embodiment, the female Luer-Lok fitting is molded (for instance using injection molding) or printed (for instance using 3D printing) as an integral part of housing 120. Alternative fittings, such as suitable friction fittings, would also be appropriate in this embodiment of insertion device 110. The fitting of nozzle 151 to housing 120 makes a substantially air-tight seal between vacuum chamber 150 and lumen 135 in main housing 120. Upon attachment of vacuum chamber 150 to main housing 120, vacuum chamber 150 communicates with lumen 135, which, in turn, communicates with the lumen of needle 140 from the distal opening 137 in housing 120 such that fluid can flow from distal end 140B of needle 140, through the needle lumen, through lumen 137, through nozzle 151, and into vacuum chamber 150. In other words, lumen 137 serves as a conduit between the lumen of needle 140 and vacuum chamber 150. Proximal end 152A of plunger 150 includes a grip 154 such as a full or partial ring. In the present embodiment, grip 154 is depicted as a partial ring. Grip 154 can be used by a clinician in when drawing back plunger 152 with his or her thumb to create a vacuum in vacuum chamber 150.

Insertion device 110 further comprises a guidewire 160. In this embodiment, guidewire 160 is disposed within guidewire housing 162, although it will be understood that guidewire housing 162 is not necessary to practice the inventions disclosed herein. In this embodiment, guidewire housing 162 is removably attached to main housing 120 at guidewire housing connector 168. Guidewire housing 162 may be retained onto handle 121A (if insertion device 110 is used in the right hand) or onto handle 121B (if insertion device 110 is used in the left hand) by the addition of a clip or other suitable retention structure (not shown) to handles 121. Guidewire housing 162 may be rigid or flexible, and of sufficient length to hold the length of guidewire 150 that is not otherwise disposed within housing 120 or needle 140. Further, guidewire housing 162 can be either removably or permanently attached to main housing 120, or could be an integral part of main housing 120. Guidewire housing 162 may additionally include cap 163. If present, cap 163 could serve a variety of purposes, including isolating guidewire 160 from the surrounding environment or to prevent guidewire 160 from being pushed out the proximal end of guidewire housing 162. Main housing 120 is configured to allow the movement of guidewire 160 from the distal end of guidewire housing 162 at or about connector 168 along guidewire feed region 164 into lumen 136 of main housing 120. Lumen 136 connects with lumen 135 in the main housing 120 at a point proximal to the connection of needle hub 137 to needle hub attachment 126. Lumen 136 is configured to receive guidewire 150 at opening 127. In this embodiment, lumen 136 is further configured to be fitted with a valve 128 between opening 127 and the point where lumen 136 joins with lumen 135. Valve 128 is configured to allow the passage of guidewire 150 but to prevent the substantial flow of air that would substantially defeat a vacuum created by the proximal movement of plunger 152 in vacuum chamber 150. It will be recognized by a person of skill in the art that while in this embodiment valve 128 is located at opening 127, valve 128 could be placed at any location along lumen 136. Moreover, it will be recognized by a person of skill in the art that a valve may not be necessary if guidewire 150 fits within lumen 136 tightly enough to prevent the substantial flow of air through lumen 136 such that the creation of a vacuum in vacuum chamber 150 is defeated. For purposes of the inventions described herein, the seal between guidewire 160 and the wall of lumen 136, whether or not value 128 is employed, should be able to maintain a pressure differential of at least about 300 mmHg, although the inventions described herein could be practiced if a pressure differential of less than 300 mmHg was maintained across lumen 136. It is contemplated that most commonly insertion device 110 would be configured to accommodate a 0.038-inch sized guidewire, although various other sized guidewires could be suitable depending on the specific applications insertion device 110 was intended.

In this embodiment, guidewire feed region 164 includes wheel 165 between guidewire housing connector 168 and opening 127 to lumen 136, over which guidewire 150 passes. Wheel 165 is disposed about an axle 166 that, in turn, is held onto housing 120 suing two opposed axle mounts 167A and 167B, on the right and left sides, respectively, of housing 120. Wheel 165 is configured to turn about axle 166. Alternatively, wheel 165 may be fixed to axle 166, and axle 166 is configured to turn within axle mounts 167A and 167B. Guidewire feed region 164 is generally configured to be accessible by the thumb of the user while gripping main housing 120 with one hand; however, the configuration may be altered in some embodiments of the present inventions such that the guidewire feed region 164 is accessible by a finger of the one hand of the user gripping main housing 120. In this embodiment, the thumb of the user can be used to advance guidewire 150 through needle 140 toward distal end 140B of needle 140 and into the targeted body space of the patient. Of course, the thumb of the user may also be used to move guidewire 150 in the opposite direction, toward proximal end 140A of needle 140, for instance if guidewire 150 needs to be retracted into the lumen of needle 140 and repositioned, or otherwise retracted from the targeted body space. Wheel 165 can serve to provide tactile feedback to the clinician while advancing (or retracting) guidewire 150, as well as to provide a raised surface against while to press guidewire 150 to assist in gripping of guidewire 160 to more efficient movement of guidewire 150.

In this embodiment, insertion device 110 includes a sheath 171 that is coaxially moveably disposed about needle 140. Sheath 171 is attached to sheath movement element 170 at sheath hub 174. Notably, sheath 171 may be permanently or removably attached to sheath hub 174. Where sheath 171 is removably attached to sheath hub 174, sheath may be detached after the placement of the guidewire in the targeted tissue so that a port can be maintained into the targeted tissue space. In this embodiment, sheath movement element 170 includes sheath movement tab 172, arms 173A and 173B, sheath hub 174, tab 175, and grooves 176A and 176B. Sheath movement tab 172 is configured to permit a user, while gripping main housing 120 with a single hand, to move sheath movement element 170 in proximal and distal directions using the thumb of the single hand. Movement of sheath movement element 170 in a distal direction would result in sheath 171 moving coaxially along needle 140 toward distal end 140B of needle 140. Further, both the length of sheath 171 and the degree of movement permitted of sheath movement element 170 is sufficient to permit the furthest movement of sheath 171 in a distal direction to cover distal end 140B of needle 140 to shield distal end 140B of needle 140. Conversely, movement of sheath movement element 170 in a distal direction would result in sheath 171 moving coaxially along needle 140 away from distal end 140B of needle 140. Continued movement of sheath movement element 170 would result in the exposure of needle distal end 140B. Movement of the sheath movement element 170 in a distal direction from the position depicted in FIG. 5 results in tab 175 of sheath movement element 170 passing over ridge 124 and resting in notch 125 of housing 120. Notch 125 is created on the proximal end by ridge 124 and on the distal end by stopper 125. The contact of tab 175 with stopper 125 arrests the distal advancement of sheath movement element 170, and therefore the extent of movement of sheath 160 in the distal direction. In use, the passage of tab 175 over ridge 124 creates tactile feedback to inform the clinician that the furthest extent of sheath 160 advancement is being reached. In addition, when tab 175 is resting in notch 123, proximal movement of sheath movement element 170 is partially restricted by ridge 124, thereby reducing the possibility of accidental retraction of sheath 171. Sheath movement element 170 is moveably attached to housing 120 by the joining of grooves 176A and 176B of sheath movement element 170 to rails 139A and 139B of housing 120.

In this embodiment of insertion device 110, sheath movement element 170 is disposed on the top 120A of housing 120 and guidewire 150 is also disposed on the top 120A of housing 120. However, it will be appreciated by persons of skill in the art that the inventions described herein can be practiced with both the sheath movement element 170 and the guidewire 150 disposed on the opposite sides of housing 120, as described elsewhere herein.

Figure 8:
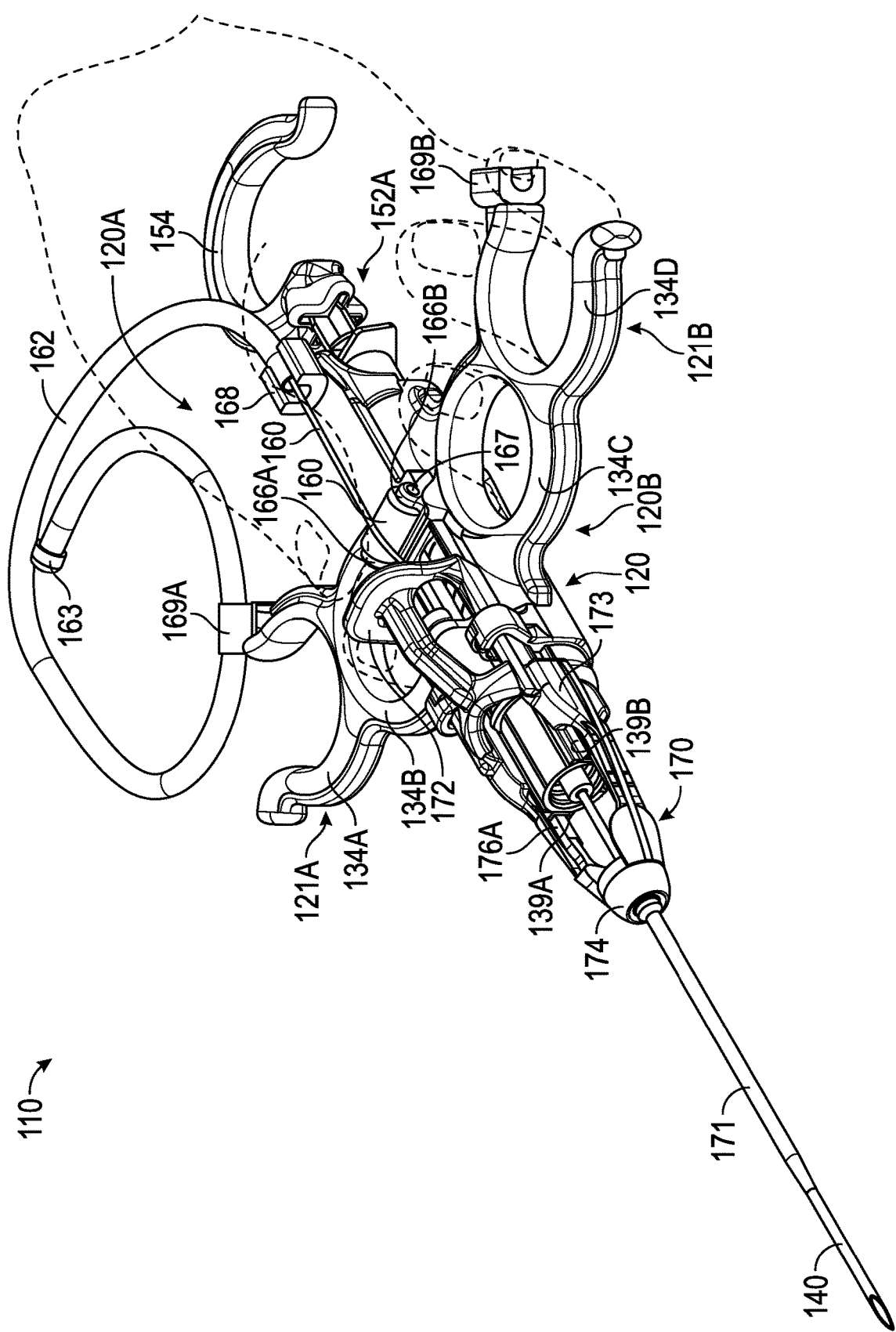
FIG. 8 illustrates a view of the embodiment depicted in FIG. 5 as held by a clinician.
Figure 9:
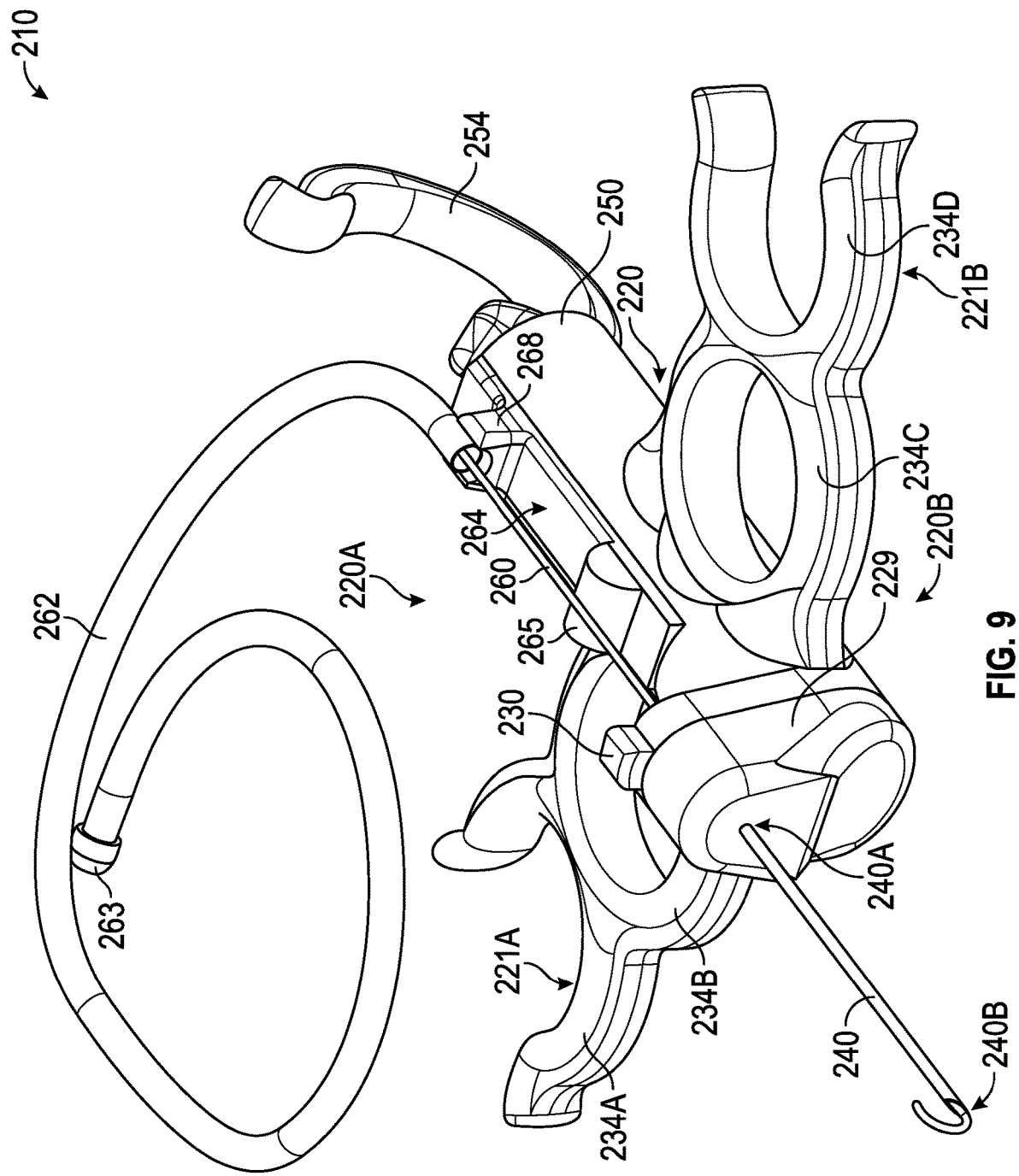
FIG. 9 illustrates a top perspective view of the insertion device in accordance with another embodiment.

As indicated above, the embodiment of the inventions disclosed herein, where the insertion device includes a sheath and finger grips such as depicted in FIGS. 5-7 can be used to perform a venous access procedure according to the inventions disclosed herein using the ultrasound-guided modified Seldinger Technique. FIG. 8 shows an example view of this embodiment in use. In use, a clinician grips the insertion device 110 in the dominant hand and an ultrasound probe (not shown) in the non-dominant hand. In a right-hand dominant user, the index finger is inserted into the closed-ring finger grip 134B on the right side (as oriented in FIGS. 5-7 from the perspective of viewing insertion device 110 from the proximal end) of main housing 120. The clinician's middle finger of the dominant hand is inserted into the closed-ring finger grip 134C on the left side of main housing 120, and the ring finger of the dominant hand is situated in the open-ring finger grip 134D on the left side of main housing 120. When prepared for use, guidewire 160 may be positioned within conduit 136 or in the lumen of needle 140, with the distal end of guidewire 160 reasonably close to, but proximal to, tip 141 of needle 140. Such pre-positioning of guidewire 160 in conduit 136 or in the lumen of needle 140 can assist in the rapid deployment of guidewire 160 into the targeted body space. However, such pre-positioning of guidewire 160 or other wire-like structure to be inserted into the targeted body space within the lumen of needle 140 is not necessary for the practice of this method.

With sheath movement element 170 in a distal position, such that the tip 141 of needle 140 is exposed, the clinician presses the tip 141 of needle 140 against a patient's skin and uses it to penetrate through tissue. While the clinician is inserting the needle, the clinician uses the ultrasound probe and the cross-sectional and longitudinal images produced by the ultrasound machine to follow the progress of needle 140 as it pierces through the tissue. Also while the clinician is inserting needle 140 through patient tissue, the clinician uses the thumb of the dominant hand to draw back plunger 152 using grip 154, thereby creating a suction in vacuum chamber 150. The suction created in vacuum chamber 150 in turn results in a suction at tip 141 of needle 140 through conduit 135. Body fluid is drawn from the region around tip 141 of needle 140, through the needle lumen, through conduit 135 and into vacuum chamber 150. When the tip 141 of needle 140 accesses and pierces the targeted vein, blood flows through the lumen of needle 140, into conduit 135 and into vacuum chamber 150. Visualization of blood in needle hub 142, conduit 135, and/or vacuum chamber 150 indicates to the clinician that the targeted vein has been reached and punctured. It will be appreciated that where this process is applied for the access of targeted body regions other than veins, the appearance of other, appropriate body fluids in needle hub 142, conduit 135, and/or vacuum chamber 150 would indicate that the particular targeted body region had been reached.

Once the targeted body region, in this example the vein, has been reached, the clinician stops moving needle 140 forward. The clinician then uses the thumb of the dominant hand to push sheath movement tab 172 to move sheath movement element 170 in a distal direction. The distal movement of sheath movement element 170 results in the distal coaxial movement of sheath 171 in a distal direction to cover tip 142 of needle 140. This deployment of sheath 170 in a distal direction to cover tip 142 of needle 140 partially secures access in the vein and tends to prevent further tissue damage by shielding the patient's tissue from the sharp tip 142 of needle 140. When sheath 170 has been advanced to cover tip 142 of needle 140, the clinician uses the thumb of the dominant hand to press guidewire 160 against roller 165 and advance guidewire 160 in a distal direction by repeatedly moving the thumb along the guidewire feed region 164 and over roller 165. As explained above, roller 165 may be easily replaced in some embodiments of the inventions disclosed herein with a protrusion, button, or other structure in guidewire feed region 164 configured to aid the clinician in advancing guidewire 160 in a distal direction and/or retracting guidewire 160 in a proximal direction.

In this manner, the clinician uses the thumb to advance guidewire 160 in a distal direction, through conduit 136 and valve 127 into the lumen of needle 140, past the tip 141 of needle 140 and ultimately past the distal end of sheath 171 into the vein or other targeted body space. Because the access device allows for single-handed venipuncture and insertion, the operator can use ultrasound imaging to visualize the needle tip while it is inside of the vein and the guidewire as it is advanced into the vein. Consequently, the risk of tissue injury diminishes. Furthermore, retaining ultrasound visibility allows the operator to ensure that the guidewire is going into the targeted vein as he inserts it. After the operator inserts the guidewire into the vein to the desired length, the access device is removed while the guidewire remains in place for dilation and catheter, sheath, or cannula insertion.

FIGS. 9-12 depict an embodiment of the inventions disclosed herein. Insertion device 210 comprises a main housing 220 that includes, for reference in these figures, a top side 220A and bottom side 220B. Main housing 220 may include handles 221A and 221B, on the right and left sides of main housing 220, respectively. Handles 221A and 221B are configured to facilitate the ergonomic gripping of insertion device 210 by a user, or clinician, with a single hand. As shown in the figures, in this embodiment, handles 221A and 221B each comprise two grips, where the grip closer to main housing 220 is a full-loop finger grip and the grip away from main housing 220 is a partial-loop finger grip. As is apparent to a person of skill in the art, handles 220A and 220B would be configured to include unequal number of grips on each side of main housing 220, and such grips may be any appropriate combination of full-loop or partial-loop grips, as well as other, non-loop type grips. Main housing 220 is comprised of thermoplastic such as polycarbonate and is transparent, although manufacture using other suitable materials will be readily apparent to a person of skill in the art. If main housing 220 is constructed of a translucent or opaque material, main housing 220 may be configured to include transparent regions (not shown) to permit the user to view the inside of vacuum chamber 250 and/or conduit 235, as will be further described below.

Figure 10:
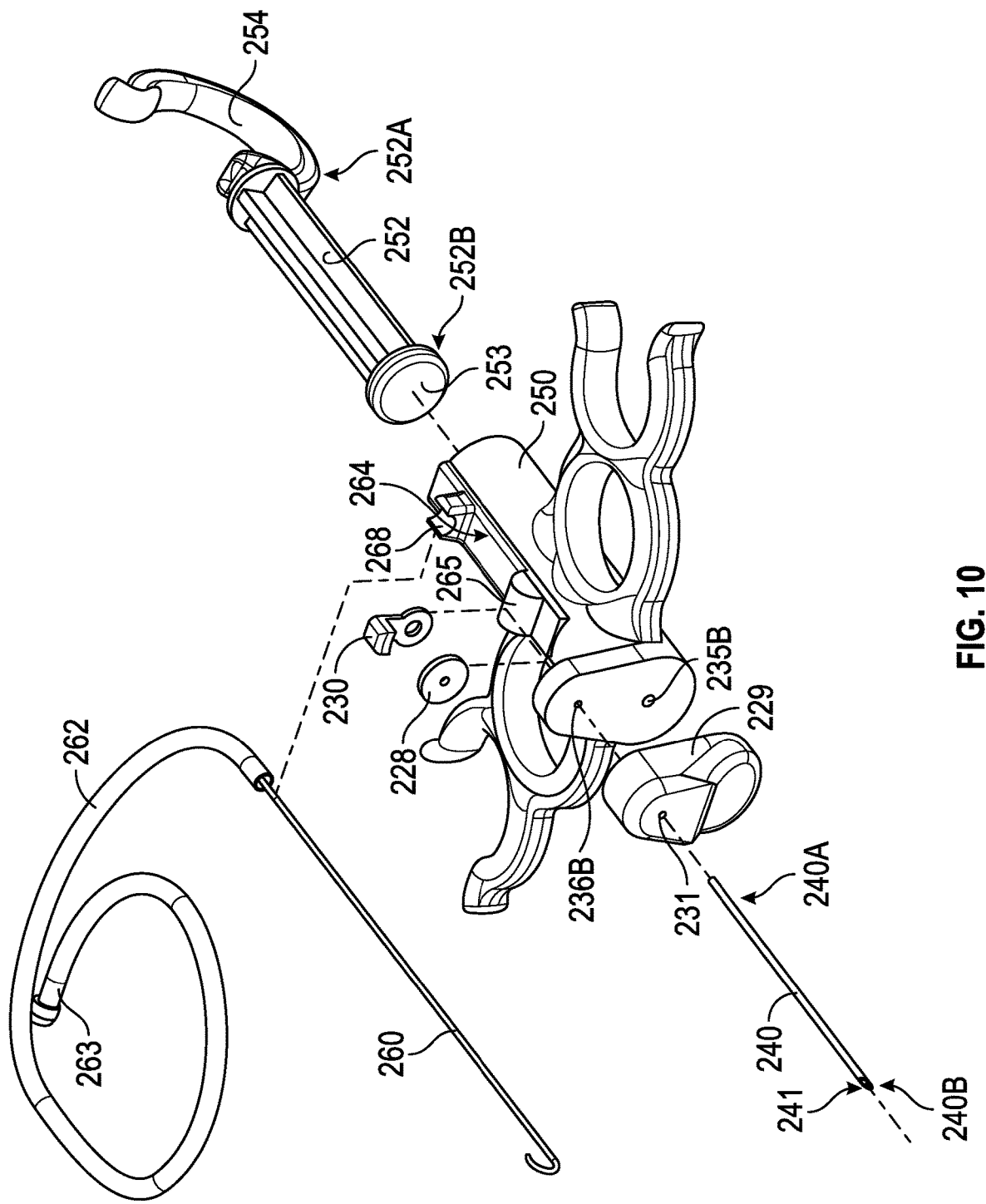
FIG. 10 illustrates a top perspective exploded view of the insertion device in accordance with the embodiment depicted in FIG. 9.
Figure 11:
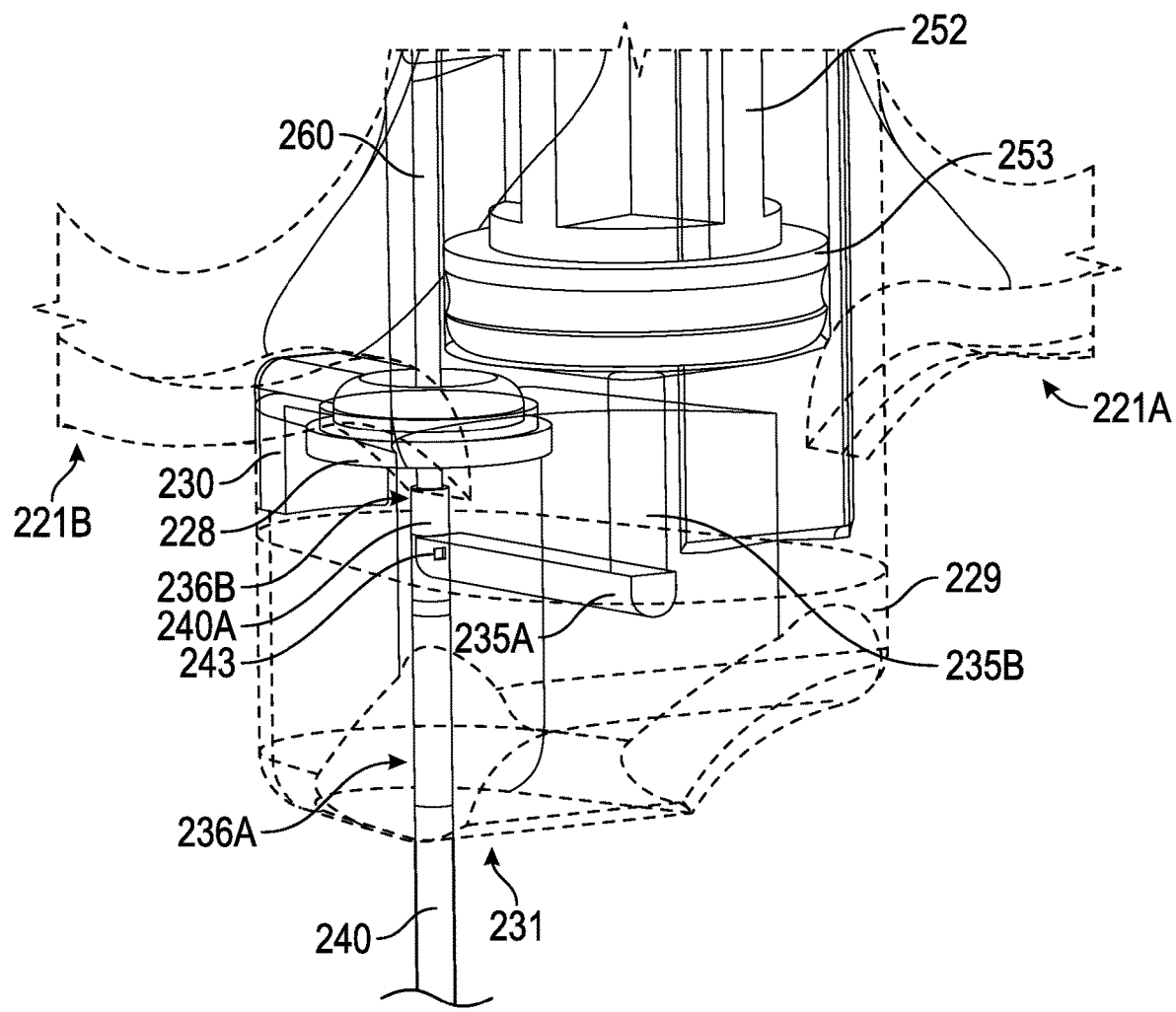
FIG. 11 illustrates a detail perspective view of a portion of the embodiment depicted in FIG. 9.
Figure 12:
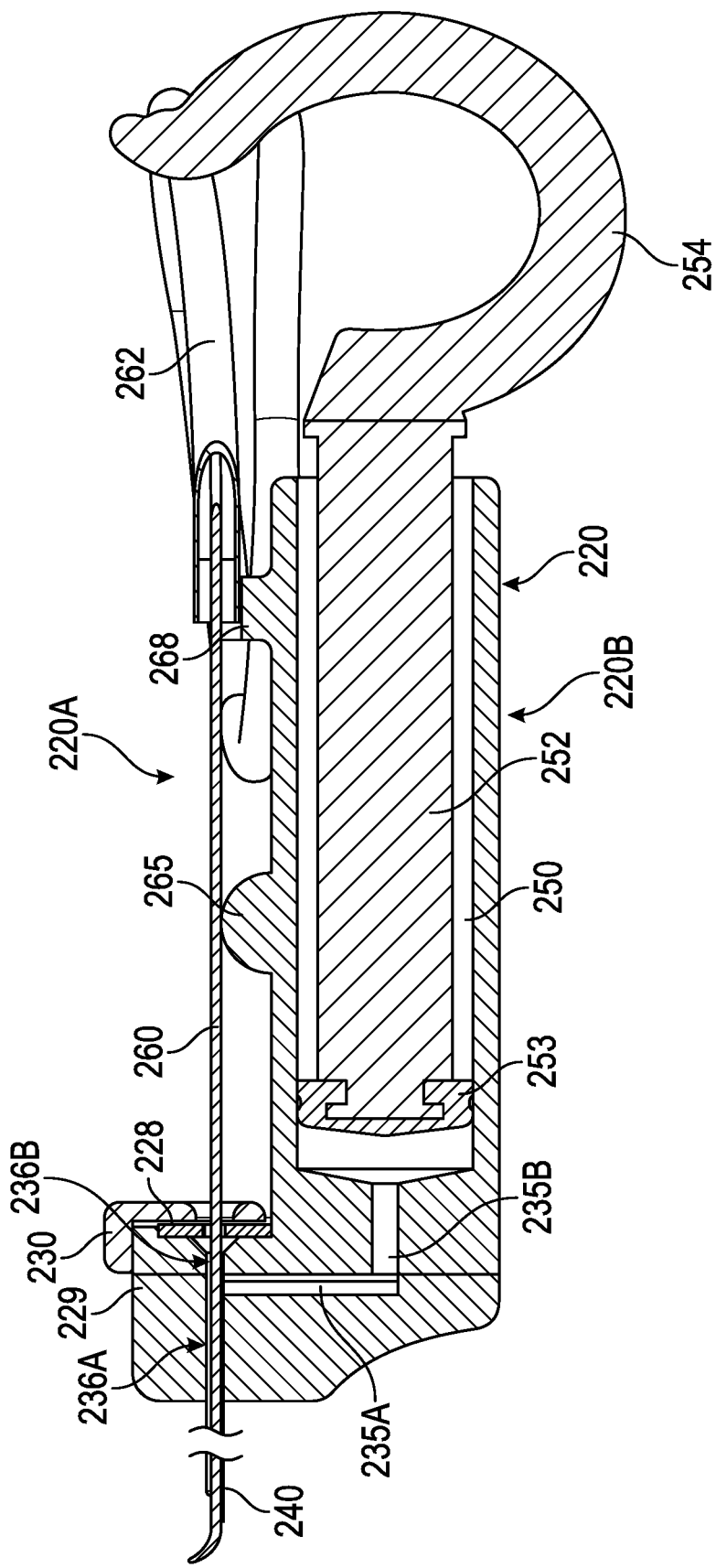
FIG. 12 illustrates a cross-sectional view of the insertion device in accordance with the embodiment depicted in FIG. 9.

Main housing 220 includes a main housing cap 229, additional details of which are depicted in FIG. 10. Main housing cap 229 includes needle attachment opening 231, conduit 236A, and channel 235A. Main housing cap 229 is formed of substantially transparent thermoplastic such as polycarbonate. However, it will be recognized that main housing cap 229 may be formed of other materials as well, and may be translucent, substantially opaque, or opaque. In the event that main housing cap 229 is not formed of material that is substantially transparent, it may be desirable to form main housing cap 229 with a clear, or substantially transparent, section, such as a window, that would permit a user to visualize contents of channel 235A while insertion device 210 is in use, in particular to allow user to visualize the presence of fluid from the targeted body space in channel 235A while aspirating into vacuum chamber 250. In this embodiment, needle attachment opening 231 is continuous with conduit 236A, which runs through main housing cap 229. When main housing cap 229 is mounted onto main housing 220, conduit 236A in main housing cap 229 is contiguous with conduit 236B in main housing 220. Main housing cap 229 can be affixed to main housing 220 using a variety of suitable methods such as, for instance, ultrasonic welds, epoxy, or resin for a permanent attachment. It will be appreciated that main housing cap 229 may also be temporarily affixed to main housing 220 using clips, screws, or other suitable means. In an instance where main housing cap 229 if temporarily affixed to main housing 220, it will be recognized by a person of skill in the art that additional seals may be deployed to ensure that conduits 235A, 235B, 236A, and 236B are substantially air-tight during use such that the necessary pressure differential, as described herein, can be maintained to permit the aspiration of body fluids from the targeted body space.

A hollow piercing structure, such as needle 240, is included in insertion device 210. Proximal end 240A of needle 240 is affixed, through needle attachment opening 231 and through conduit 236A of main housing cap 229, into conduit 236B of main housing 220. Various methods of affixing needle 240 to main housing cap 229 and main housing 220 will be appreciated, including plastic cement, appropriate epoxy, and ultraviolet curing. However, to practice the inventions disclosed herein, it is not necessary that needle 240 be permanently affixed to main housing cap 229 and/or main housing 220. Indeed, it will be appreciated that in some embodiments of the inventions disclosed herein, it may be desirable for needle 240 be to movably and/or removably attached to main housing cap 229 and/or main housing 220 so that, for example, needle 240 can be changed or for example, the orientation of needle 240 can be altered so that the direction of bevel 241 of needle 240 can be adjusted relative to the orientation of housing 220.

The region around proximal end 240A of needle 240 includes an opening 243 along the shaft of needle 240 that is in communication with the lumen of needle 240. Opening 243 on needle 240 is oriented to communicate with conduit 235A to permit the flow of aspirated body fluids from the region of the distal end 240B of needle 240, through the lumen of needle 240, and into conduit 235A. Such aspirated body fluids would be permitted to flow through conduit 235A into conduit 235B and ultimately into vacuum chamber 250.

Insertion device 210 further includes a vacuum chamber 250 configured to receive plunger 252. Vacuum chamber 250 is in communication with conduits 235B and 235A such that pressure differential created in vacuum chamber 250 will create a suction passing through conduit 235 into the lumen of needle 240, to permit the aspiration of fluids through the distal tip 240B of needle 240. Plunger 252 includes a proximal end 252A and a distal end 252B. Distal end 252B of plunger 252 includes a head 253 that has a size and shape sufficient to create a substantially air-tight annular seal between the edge of head 253 and the side walls of vacuum chamber 250. Proximal end 252A of plunger 252 includes a handle 254 that is configured to receive the thumb or finger of a user while using insertion device 210. Handle 254 in this embodiment is depicted as an open ring; however, it will be appreciated that handle 254 can be configured as a closed ring, a tab, or any other suitable design that will permit the user to draw back plunger 252 in vacuum chamber 250 with a digit of the single hand used to hold insertion device 210 while in use. It will also be appreciated that while vacuum chamber 250 is depicted in this embodiment as a contiguous part of main housing 220, vacuum chamber 250 could be a separate structure, such as a syringe, that may be coupled to main housing 220 in a substantially air-tight manner to permit the creation of a pressure differential sufficient to aspirate fluids from the targeted body cavity of a patient.

Insertion device 210 is further configured to include guidewire 260. In this embodiment, the proximal region of guidewire 260 is disposed within guidewire housing 262, which, in turn, is removably attached to main housing 250 at guidewire housing connector 268. Guidewire housing 262 may be either rigid or flexible, and may be permanently or removably attached to main housing 220. Further, as shown in the Figures, guidewire housing 262 may be configured to receive cap 263. Cap 263 can serve to retain guidewire 260 in guidewire housing 262, as well as to isolate guidewire 260 from potential contaminants in the surrounding environment.

Guidewire 260 spans guidewire feed region 264. Main housing 220 is configured to receive the distal end of guidewire 260 in conduit 236. In this embodiment, valve 228 is provided and configured to permit guidewire 260 to pass through it prior to entering conduit 236. As shown, valve 228 is held in place on main housing 220 by use of cap 230. Cap 230 is affixed to main housing 220 as a snap-fit assembly. Like valve 228, cap 230 is configured to permit guidewire 260 to pass through it prior to entering conduit 236 as shown, for example, in FIG. 12. It will be appreciated that cap 230 may be affixed to main housing 220 as a snap-fit assembly or in a variety of other means, such as epoxy, plastic cement, or ultra-violet curing. Additionally, while the figures depicting this embodiment show valve 228 at a proximal edge of main housing 228, it will be understood that valve 228 may be placed not only at the entrance of conduit 236, but alternatively at any location along conduit 236. For example, valve 228 could be placed between a distal end of main housing 220 and a proximal end of main housing cap 229. In this latter configuration, cap 230 would not be necessary to hold valve 228 in place.

Valve 228 serves in insertion device 210 to prevent the substantial movement of air through conduit 236B such that the pressure differential created by the proximal movement of plunger 252 in vacuum chamber 250 would be defeated. Preferably, valve 228 would provide an air-tight seal around the guidewire of at least about 300 mmHg of pressure. Valve 228 may be pressure-sensitive. However, it will be appreciated that the function of the inventions disclosed herein, and specifically the aspiration of fluid from a targeted body space through the lumen of needle 240 and ultimately into vacuum chamber 250, the inventions disclosed herein could be practiced with a vacuum of more or less than about 300 mmHg pressure, depending on the specific application and design of the insertion tool 210. It will also be apparent that valve 228 may not be necessary to maintain the necessary vacuum, if the entry to conduit 236B is sized so that the guidewire itself creates a sufficient seal to substantially prevent the flow of air through conduit 236B during aspiration. It will be apparent to persons of skill in that art that other suitable means to maintain pressure differential across conduit 236 may be employed. For instance, conduit 236 may be configured with two valves, in which case guidewire 260 (or other wire-like structure to be inserted into the targeted body space) can be preloaded into conduit 236 with the distal end of guidewire 260 positioned between the two valves.

When insertion tool 210 is prepared for use, it may be beneficial that guidewire 260 is configured within needle 240, with the distal end of guidewire 260 close to distal end 240B of needle 240. The tip of the distal end of guidewire 260, however, should not extend through the distal end 240B of needle 240, and should remain clear of bevel 241 of needle 240. However, when the distal tip of guidewire 260 is placed near the distal end 240B of needle 240 when insertion device 210 is prepared for use, the user is able to more rapidly advance guidewire 260 into the targeted body space, thus securing access to the targeted body space, as soon as puncture of the targeted body space is confirmed, such as through the aspiration of appropriate body fluids through conduit 235 and/or into vacuum chamber 250.

Figure 13:
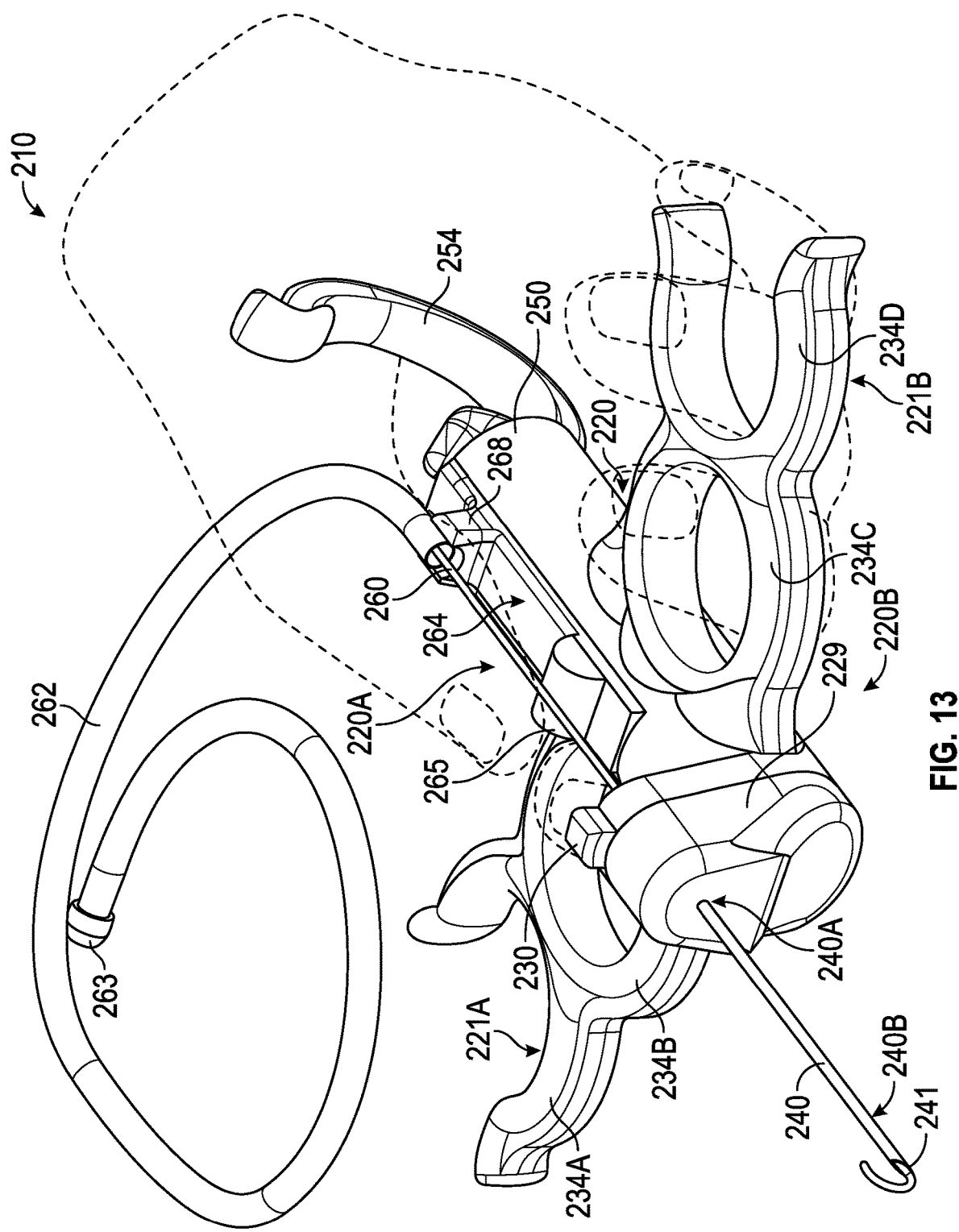
FIG. 13 illustrates a view of the embodiment depicted in FIG. 9 as held by a clinician.

The use of the inventions disclosed herein is not limited to devices that include a sheath. For instance, the embodiment depicted in FIGS. 9-12 can be used to perform a venous access procedure using the ultrasound-guided modified Seldinger Technique according to the invention described herein. FIG. 13 shows an example view of this embodiment in use. In use, a clinician grips the insertion device 210 in the dominant hand and an ultrasound probe (not shown) in the non-dominant hand. In a right-hand dominant user, the index finger is inserted into the closed-ring finger grip 234B on the right side (as oriented in FIGS. 9-12 from the perspective of viewing insertion device 210 from the proximal end) of main housing 220. The clinician's middle finger of the dominant hand is inserted into the closed-ring finger grip 234C on the left side of main housing 220, and the ring finger of the dominant hand is situated in the open-ring finger grip 234D on the left side of main housing 220. When prepared for use, guidewire 260 may be positioned within conduit 236, with the distal end of guidewire 260 reasonably close to, but proximal to, tip 241 of needle 240. Such pre-positioning of guidewire 260 in the lumen of needle 240 can assist in the rapid deployment of guidewire 260 into the targeted body space. However, such pre-positioning of guidewire 260 within the lumen of needle 240 is not necessary for the practice of this method.

The clinician presses the tip 241 of needle 240 against a patient's skin and uses it to penetrate through tissue. While the clinician is inserting the needle, the clinician uses the ultrasound probe and the image produced by the ultrasound machine to follow the progress of needle 240 as it pierces through the tissue. Also while the clinician is inserting needle 240 through patient tissue, the clinician uses the thumb of the dominant hand to draw back plunger 252 using grip 254, thereby creating a suction in vacuum chamber 250. The suction created in vacuum chamber 250 in turn results in a suction at tip 241 of needle 240 through conduit 235. Body fluid is drawn from the region around tip 241 of needle 240, through the needle lumen, through conduit 235 and into vacuum chamber 250. When the tip 241 of needle 240 accesses and pierces the targeted vein, blood flows through the lumen of needle 240, into conduit 235A and 235B and into vacuum chamber 250. Visualization of blood in conduit 235A, conduit 235B, and/or vacuum chamber 250 indicates to the clinician that the targeted vein has been reached and punctured. It will be appreciated that where this process is applied for the access of targeted body regions other than veins, the appearance of other, appropriate body fluids in conduit 235A conduit 235B, and/or vacuum chamber 250 would indicate that the particular targeted body region had been reached.

Once the targeted body region, in this example the vein, has been reached, the clinician stops moving needle 240 forward. The clinician uses the thumb of the dominant hand to press guidewire 260 against protrusion 265 and advance guidewire 260 in a distal direction by repeatedly moving the thumb along the guidewire feed region 264 and over protrusion 265. As explained above, protrusion 265 may be easily replaced in some embodiments of the inventions disclosed herein with a wheel, button, or other structure in guidewire feed region 264 configured to aid the clinician in advancing guidewire 260 in a distal direction and/or retracting guidewire 260 in a proximal direction.

In this manner, the clinician uses the thumb to advance guidewire 260 in a distal direction, through conduit 236 and valve 228 into the lumen of needle 240, past the tip 241 of needle 240 and into the vein or other targeted body space. Because the access device allows for single-handed venipuncture and insertion, the operator can use ultrasound imaging to visualize the needle tip while it is inside of the vein and the guidewire as it is advanced into the vein. Consequently, the risk of tissue injury diminishes. Furthermore, retaining ultrasound visibility allows the operator to ensure that the guidewire is going into the targeted vein as he inserts it. After the operator inserts the guidewire into the vein to the desired length, the access device is removed while the guidewire remains in place for dilation and catheter, sheath, or cannula insertion.

Figure 14:
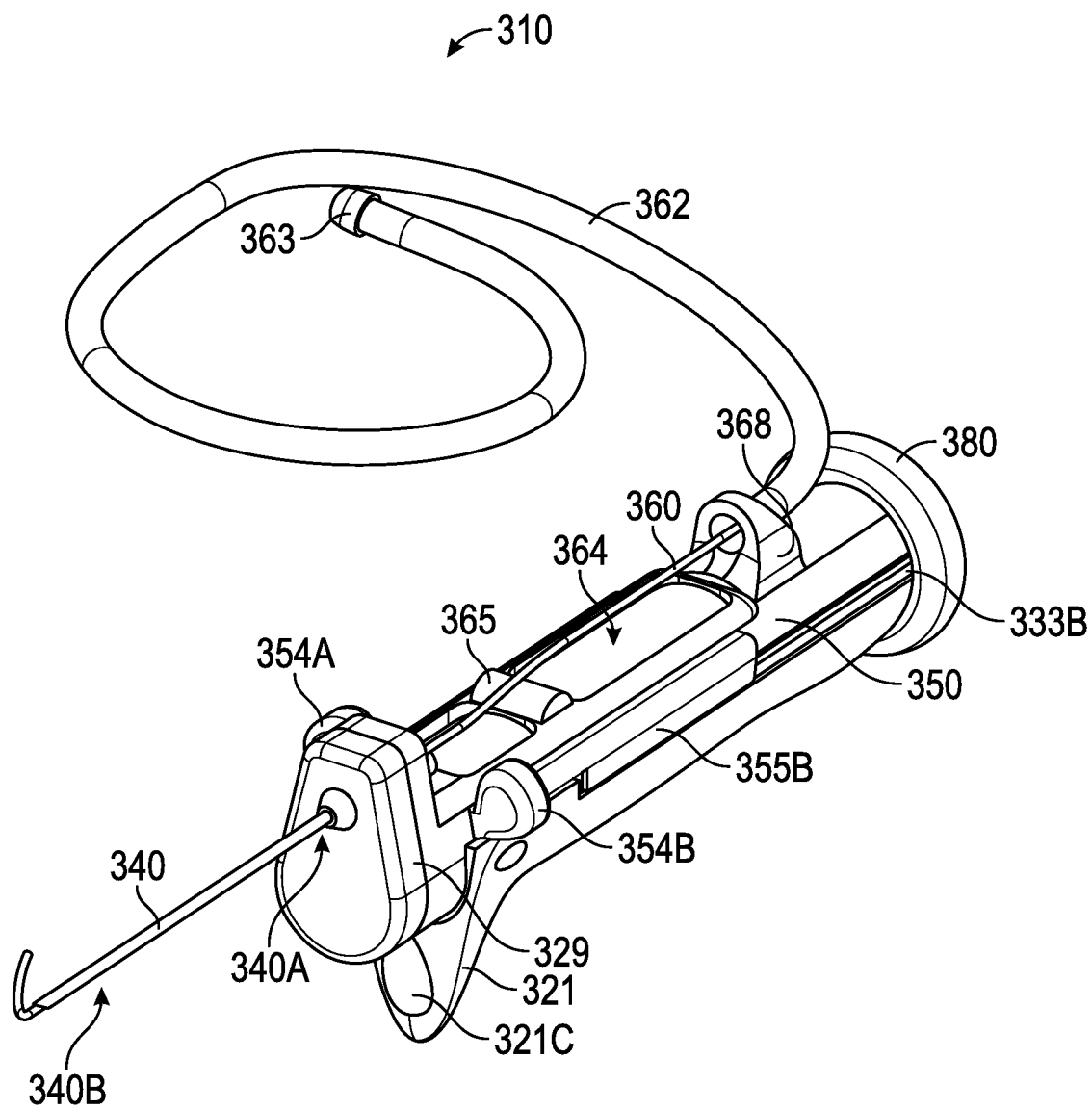
FIG. 14 illustrates a top perspective view of the insertion device in accordance with another embodiment.
Figure 15:
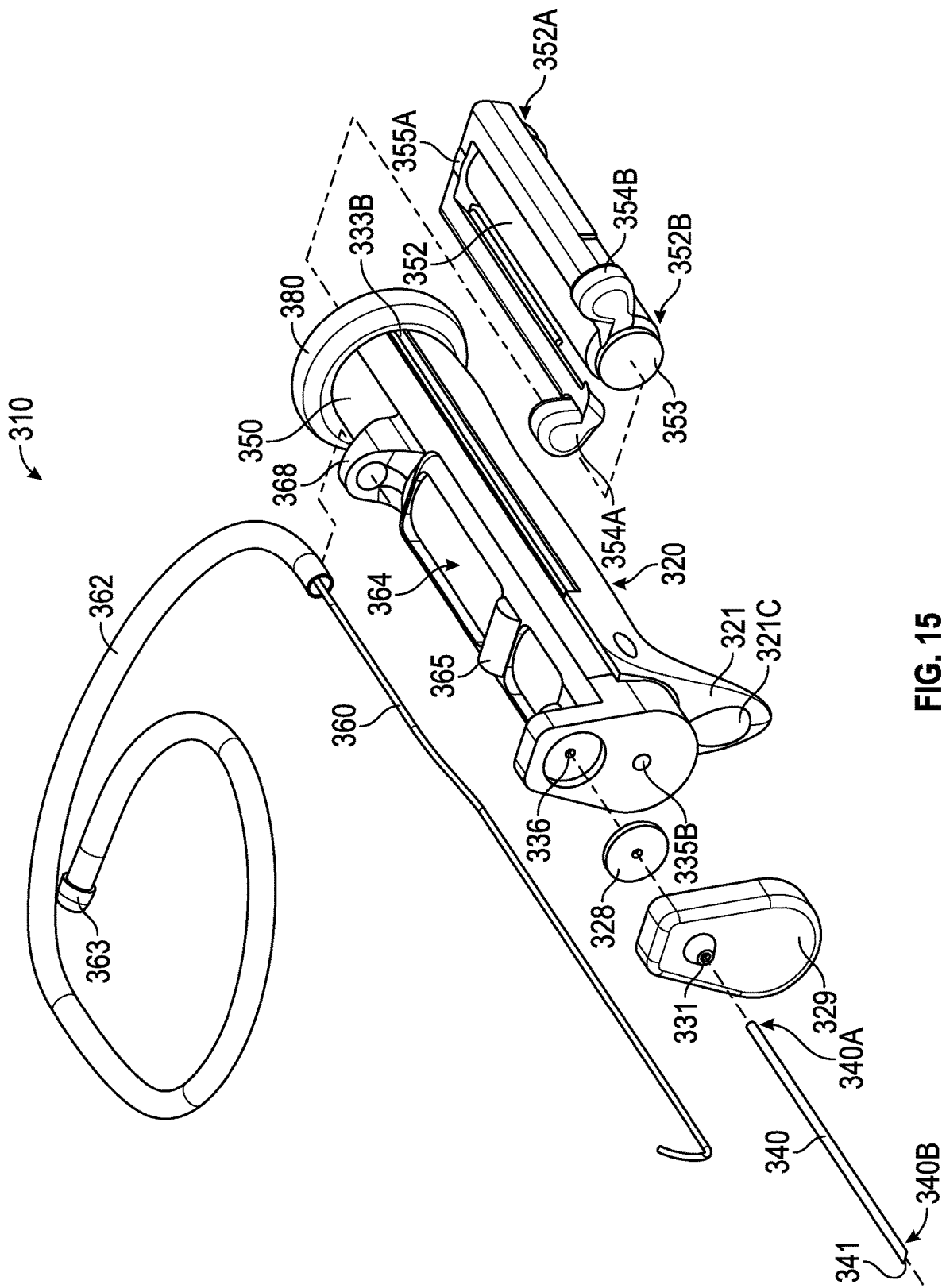
FIG. 15 illustrates a top perspective exploded view of the insertion device in accordance with the embodiment depicted in FIG. 14.
Figure 16:
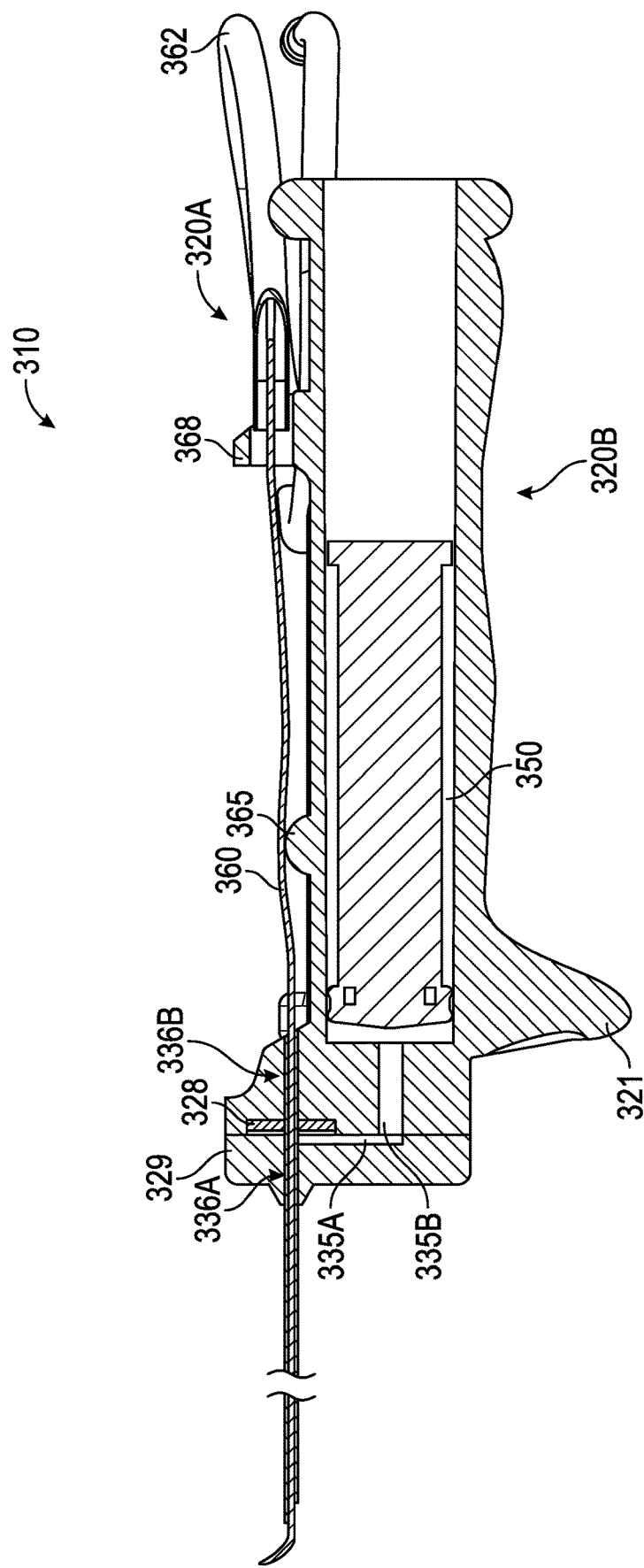
FIG. 16 illustrates a side cross-sectional view of the insertion device in accordance with the embodiment depicted in FIG. 14.

FIGS. 14-16 depict an embodiment of the invention, insertion device 310. As has been explained, one of the benefits of the inventions disclosed herein is to permit a clinician, or user, to insert an object, such as a guidewire, into a targeted body space to secure access to the targeted body space using one hand. With the inventions disclosed here, the clinician can puncture the body of the patient with a hollow piercing object, such as a needle, confirm access to the targeted body space by aspirating body fluid through the hollow piercing structure, and advance a guidewire to secure access into the targeted body space, all using a single hand. Typically, the dominant hand of the clinician will be used to secure access to the targeted body space, while the clinician's other hand is used to hold an ultrasound probe or other visualization tool to watch the advancement of the hollow piercing structure into the patient, watch the movement of the hollow piercing structure within the patient, and watch the advancement of the guidewire into the patient. As the insertion devices that embody the inventions described herein are configured to be operated by one hand, ergonomic considerations should be evaluated when designing insertion tools according to the inventions described herein. Considering the present embodiment of the inventions, insertion device 310 is configured to be held by clinician using a single hand with a generally overhand grip. Comparing the present embodiment to other possible embodiments of the inventions described herein, it will be clear to a person of skill that the described inventions can be practiced using a variety of configurations and ergonomically beneficial designs. Such designs can be configured to be used in the right hand, in the left hand, or in either the right hand or the left hand. It will be clear that there are certain economic and practical benefits that can be obtained by employing the disclosed inventions in ambidextrous configurations, i.e., configurations that be used in either the right hand or the left hand.

The embodiment depicted in FIGS. 14-16, like other embodiments disclosed herein, is configured to be used in either the right hand or the left hand of a clinician. As shown, insertion device 310 includes main housing 320. Main housing 320, for reference in the figures, has a top side 320A and a bottom side 320B. Main housing 320 includes handle 321 toward the distal end of main housing 320, extending from bottom side 320B and main housing 320. Handle 321 is used to facilitate the gripping of insertion device 310 using a single hand. Typically, insertion device 310 is gripped using only the dominant hand of a clinician, or user, as will be described in more detail below. Handle 321 can be configured using a variety of arrangements. In this embodiment, handle 321 is preferably configured to allow the clinician to grip the distal end of handle 321 with either the middle finger or the index finger of the dominant hand. In the present embodiment, main housing 320 is composed of thermoplastic such as polycarbonate and is substantially transparent. Construction of main housing 320 using material that is substantially transparent facilitates the visualization by the clinician of body fluids that are aspirated into various portions of main housing 320, as will be explained in further detail below. If main housing 320 is made of a substantially non-transparent material, such as a substantially translucent or substantially opaque thermoplastic, it may be desirable to include cut-out or other window-type areas in housing 320 to permit the clinician to visualize into various conduits (such as conduit 335) and/or vacuum chamber 350 during use as will be explained in further detail below. The proximal end of main housing 320, in this embodiment, has a rounded end that may increase grip stability and comfort in the hand of the user. In addition, the bottom 320B of main housing 320 is configured to have a comfort grip shape that can add to stability and comfort in the hand of the user.

Main housing 320 includes a main housing cap 329. Main housing cap 329 includes needle attachment opening 331, conduit 336A, and channel 335A. Main housing cap 329 is formed of substantially transparent thermoplastic such as polycarbonate. However, it will be recognized that main housing cap 329 may be formed of other materials as well, and may be translucent, substantially opaque, or opaque. In the event that main housing cap 329 is not formed of material that is substantially transparent, it may be desirable to form main housing cap 329 with a clear, or substantially transparent, section, such as a window, that would permit a user to visualize contents of channel 335A while insertion device 310 is in use, in particular to allow user to visualize the presence of fluid from the targeted body space in channel 335A while aspirating into vacuum chamber 350. In this embodiment, needle attachment opening 331 is continuous with conduit 336A, which runs through main housing cap 329. When main housing cap 329 is mounted onto main housing 320, conduit 336A in main housing cap 329 is contiguous with conduit 336B in main housing 320. Main housing cap 329 can be affixed to main housing 320 using a variety of suitable methods such as, for instance, ultrasonic welds, epoxy, or resin for a permanent attachment. It will be appreciated that main housing cap 329 may also be temporarily affixed to main housing 320 using clips, screws, or other suitable means. In an instance where main housing cap 329 is temporarily affixed to main housing 320, it will be recognized by a person of skill in the art that additional seals may be deployed to ensure that conduits 335A, 335B, 336A, and 336B are substantially air-tight during use such that the necessary pressure differential, as described herein, can be maintained to permit the aspiration of body fluids from the targeted body space.

A hollow piercing structure, such as needle 340, is included in insertion device 310. Proximal end 340A of needle 340 is affixed, through needle attachment opening 331 into conduit 336A of main housing cap 329. Various methods of affixing needle 340 to main housing cap 329 and main housing 320 will be appreciated, including plastic cement, appropriate epoxy, and ultraviolet cured cement. However, to practice the inventions disclosed herein, it is not necessary that needle 340 be permanently affixed to main housing cap 329 and/or main housing 320. Indeed, it will be appreciated that in some embodiments of the inventions disclosed herein, it may be desirable for needle 340 be to movably and/or removably attached to main housing cap 329 and/or main housing 320 so that, for example, needle 340 can be changed or for example, the orientation of needle 340 can be altered so that the direction of bevel 341 of needle 340 can be adjusted relative to the orientation of housing 320. Changes to the orientation of bevel 341 of needle 340 can be particularly useful when adapting insertion device 310 for ambidextrous use or for the personal preference of bevel 341 orientation of a clinician.

FIG. 16 depicts the proximal end 340A of needle 340 terminating within conduit 336A. It should be noted, however, that proximal end 340A of needle 340 could be extended into conduit 336B. With such a design, needle 340 should be configured so that the region around proximal end 340A of needle 340 includes an opening (not shown) along the shaft of needle 340 that is in communication with the lumen of needle 340. This opening on needle 340 is oriented to communicate with conduit 335A to permit the flow of aspirated body fluids from the region of the distal end 340B of needle 340, through the lumen of needle 340, and into conduit 335A. Such aspirated body fluids would be permitted to flow through conduit 335A into conduit 335B and ultimately into vacuum chamber 350.

Insertion device 310 further includes vacuum chamber 350 configured to receive plunger 352. Vacuum chamber 350 is in communication with conduits 335B and 335A such that pressure differential created in vacuum chamber 350 will create a suction passing through conduit 335 into the lumen of needle 340, to permit the aspiration of fluids through the distal tip 340B of needle 340. Plunger 352 includes a proximal end 352A and a distal end 352B. Distal end 352B of plunger 352 includes a head 353 that has a size, shape, and composition sufficient to create a substantially air-tight annular seal between the edge of head 353 and the side walls of vacuum chamber 350. Distal end 352B of plunger 352 also includes handles 354A and 354B that are configured to receive a finger of the user while using insertion device 310. Handles 354A and 354B are contiguous with rails 355A and 355B, respectively. As depicted in FIG. 15, rails 355A and 355B are part of a continuous structure in this embodiment that wraps around the proximal end 352A and plunger 352. Rails 355A and 355B fit into channels 333A and 333B, respectively, in vacuum chamber 350. It will be noted that the attachment of handles 354A and 354B to the distal end 352B and plunger 352 is made so that handles 354A and 354B do not interfere with the seal between head 353 of plunger 352 and the interior surface of vacuum chamber 350. Channels 333A and 333B are blocked at the proximal end of vacuum chamber 350 by the addition of ring 380. Also as shown in FIGS. 14 and 15, the distal-facing ends of handles 354A and 354B are configured with finger dimples in which the finger of the user can rest to increase grip stability and comfort.

Insertion device 310 is further configured to include guidewire 360. In this embodiment, the proximal region of guidewire 360 is disposed within guidewire housing 362, which, in turn, is removably attached to main housing 320 at guidewire housing connector 368. Guidewire housing 362 may be either rigid or flexible, and may be permanently or removably attached to main housing 320. Further, as shown in the Figures, guidewire housing 362 may be configured to receive cap 363. Cap 363 can serve to retain guidewire 360 in guidewire housing 362, as well as to isolate guidewire 360 from potential contaminants in the surrounding environment.

Guidewire 360 spans guidewire feed region 364. Main housing 320 is configured to receive the distal end of guidewire 360 in conduit 336. In this embodiment, valve 328 is provided and configured to permit guidewire 360 to pass through it prior to entering conduit 336. As shown, valve 328 seated in valve seat 344 and held in place at least by main housing cap 329. Valve 328 is configured to allow guidewire 360 to pass through it prior to entering conduit 336B.

Valve 328 serves in insertion device 310 to prevent the substantial movement of air through conduit 336B such that the pressure differential created by the proximal movement of plunger 352 in vacuum chamber 350 would be defeated. Preferably, valve 328 would provide an air-tight seal around the guidewire of at least about 300 mmHg of pressure. However, it will be appreciated that the function of the inventions disclosed herein, and specifically the aspiration of fluid from a targeted body space through the lumen of needle 340 and ultimately into vacuum chamber 350, the inventions disclosed herein could be practiced with a vacuum of more or less than about 300 mmHg pressure, depending on the specific application and design of the insertion tool 310. It will also be apparent that valve 328 may not be necessary to maintain the necessary vacuum, if the entry to conduit 336B is sized so that the guidewire itself creates a sufficient seal to substantially prevent the flow of air through conduit 336B during aspiration.

When insertion tool 310 is prepared for use, it may be beneficial to use, depending on the specific application, that guidewire 360 is disposed within needle 340, with the distal end of guidewire 360 close to distal end 340B of needle 340. The tip of the distal end of guidewire 360, however, should not extend through the distal end 340B of needle 340, and should remain clear of bevel 341 of needle 340. However, when the distal tip of guidewire 360 is placed near the distal end 340B of needle 340 when insertion device 310 is prepared for use, the user is able to more rapidly advance guidewire 360 into the targeted body space, thus securing access to the targeted body space, as soon as puncture of the targeted body space is confirmed, such as through the aspiration of appropriate body fluids through conduit 335 and/or into vacuum chamber 350.

Figure 17:
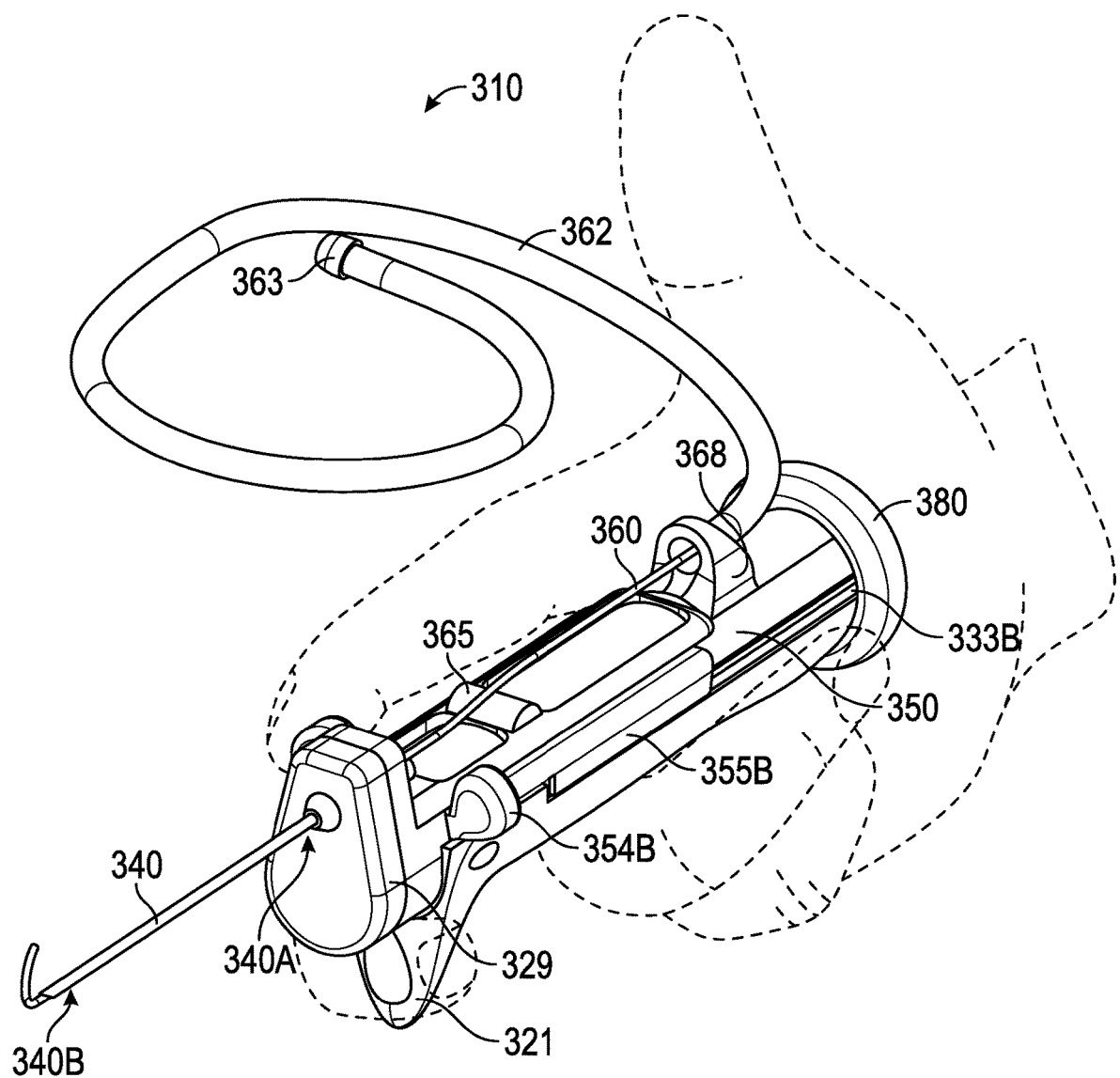
FIG. 17 illustrates a view of the embodiment depicted in FIG. 14 as held by a clinician.

As indicated above, the embodiment of the inventions disclosed herein, such as the insertion device 310 as depicted in FIGS. 14-16, can be used to perform a venous access procedure using the ultrasound-guided modified Seldinger Technique, employing the inventions disclosed herein. FIG. 17 shows an example view of this embodiment in use. When prepared for use, guidewire 360 may be positioned within conduit 336, with the distal end of guidewire 360 reasonably close to, but proximal to, tip 341 of needle 340. Such pre-positioning of guidewire 360 in the lumen of needle 340 can assist in the rapid deployment of guidewire 360 into the targeted body space. However, such pre-positioning of guidewire 360 within the lumen of needle 340 is not necessary for the practice of this method.

A clinician grasps insertion device 310 in the dominant hand and an ultrasound probe (not shown) in the non-dominant hand. In particular, the clinician grasps housing 320 of insertion device 310 in the palm of the dominant hand with the middle finger of that hand around handle 321 and optionally the tip of the middle finger positioned in dimple 321C. The index finger of the dominant hand is positioned on, for a right-hand dominant user, grip 354A. The thumb of the dominant hand can be positioned near guidewire feed region 364. The clinician presses the tip 341 of needle 340 against a patient's skin and uses it to penetrate through tissue. While the clinician is inserting the needle, the clinician uses the ultrasound probe and the image produced by the ultrasound machine to follow the progress of needle 340 as it pierces through the tissue. Also, while the clinician is inserting needle 340 through patient tissue, the clinician uses the index finger of the dominant hand to draw back plunger 352 using grip 354A, thereby creating a suction in vacuum chamber 250.

Figure 18:
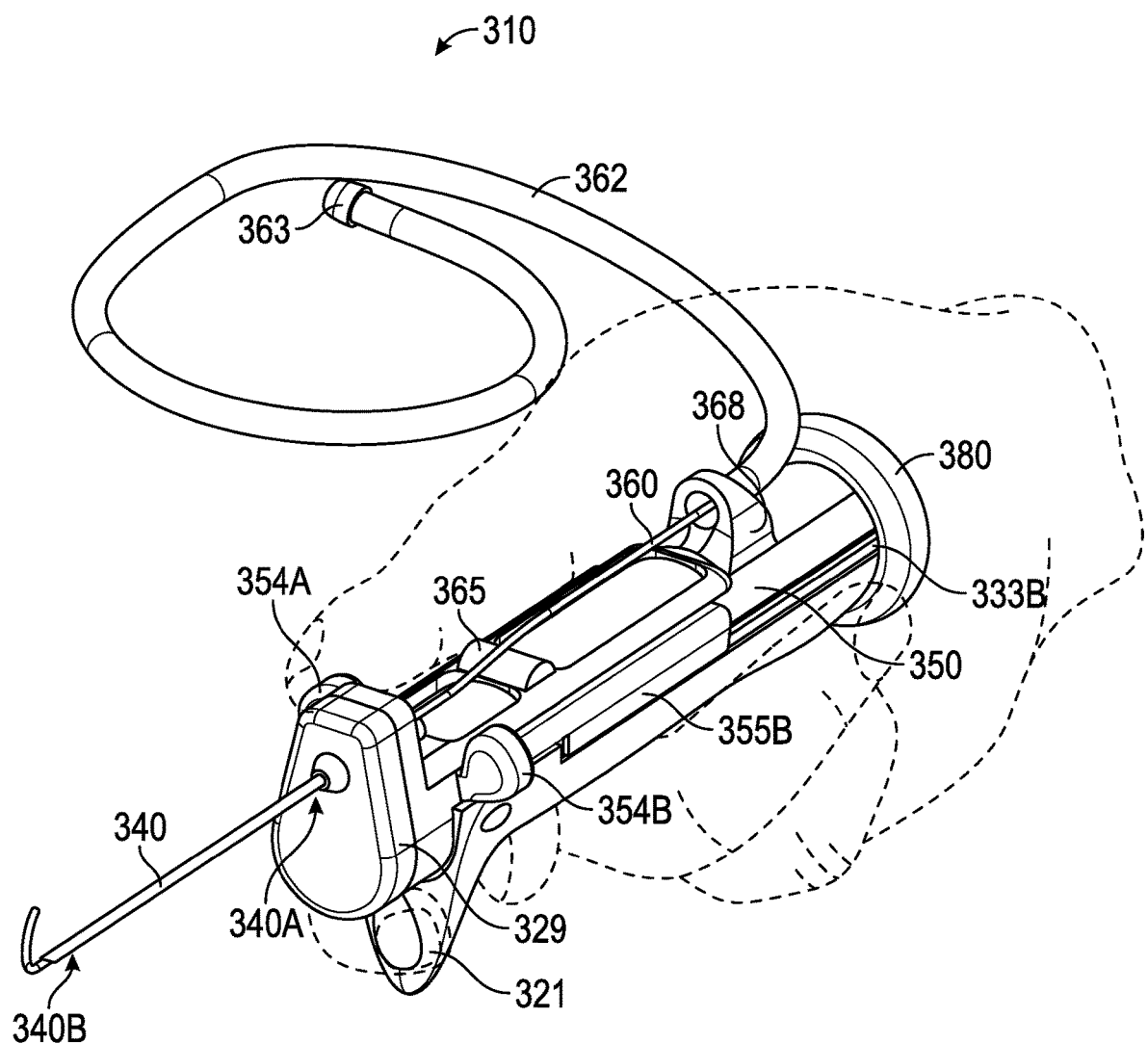
FIG. 18 illustrates a view of the embodiment depicted in FIG. 14 as held by a clinician using an alternative finger placement.

Alternatively, and as shown in FIG. 18, a clinician may grasp insertion device 310 in the palm of the dominant hand with the index finger of that hand around handle 321 and optionally the tip of the index finger positioned in dimple 321C. The thumb of the dominant hand is positioned on, for a right-hand dominant user, grip 354A. The clinician presses the tip 341 of needle 340 against a patient's skin and uses it to penetrate through tissue. While the clinician is inserting the needle, the clinician uses the ultrasound probe and the image produced by the ultrasound machine to follow the progress of needle 340 as it pierces through the tissue. Also, while the clinician is inserting needle 340 through patient tissue, the clinician uses the thumb of the dominant hand to draw back plunger 352 using grip 354A, thereby creating a suction in vacuum chamber 350.

The suction created in vacuum chamber 350 in turn results in a suction at tip 341 of needle 340 through conduit 335. Body fluid is drawn from the region around tip 341 of needle 340, through the needle lumen, through conduit 335 and into vacuum chamber 350. When the tip 341 of needle 340 accesses and pierces the targeted vein, blood flows through the lumen of needle 340, into conduit 335A and 335B and into vacuum chamber 350. Visualization of blood in conduit 335A, conduct 335B, and/or vacuum chamber 350 indicates to the clinician that the targeted vein has been reached and punctured. It will be appreciated that where this process is applied for the access of targeted body regions other than veins, the appearance of other, appropriate body fluids in conduit 335A conduit 335B, and/or vacuum chamber 350 would indicate that the particular targeted body region had been reached.

Once the targeted body region, in this example the vein, has been reached, the clinician stops moving needle 340 forward. The clinician uses the thumb of the dominant hand to press guidewire 360 against protrusion 365 and advance guidewire 360 in a distal direction by repeatedly moving the thumb along the guidewire feed region 364 and over protrusion 365. As explained above, protrusion 365 may be easily replaced in some embodiments of the inventions disclosed herein with a wheel, button, or other structure in guidewire feed region 364 configured to aid the clinician in advancing guidewire 360 in a distal direction and/or retracting guidewire 360 in a proximal direction.

In this manner, the clinician uses the thumb to advance guidewire 360 in a distal direction, through conduit 336 and valve 328 into the lumen of needle 340, past the tip 341 of needle 340 and into the vein or other targeted body space. Because the access device allows for single-handed venipuncture and insertion, the operator can use ultrasound imaging to visualize the needle tip while it is inside of the vein and the guidewire as it is advanced into the vein. Consequently, the risk of tissue injury diminishes. Furthermore, retaining ultrasound visibility allows the operator to ensure that the guidewire is going into the targeted vein as he inserts it. After the operator inserts the guidewire into the vein to the desired length, the access device is removed while the guidewire remains in place for dilation and catheter, sheath, or cannula insertion.

Figure 19:
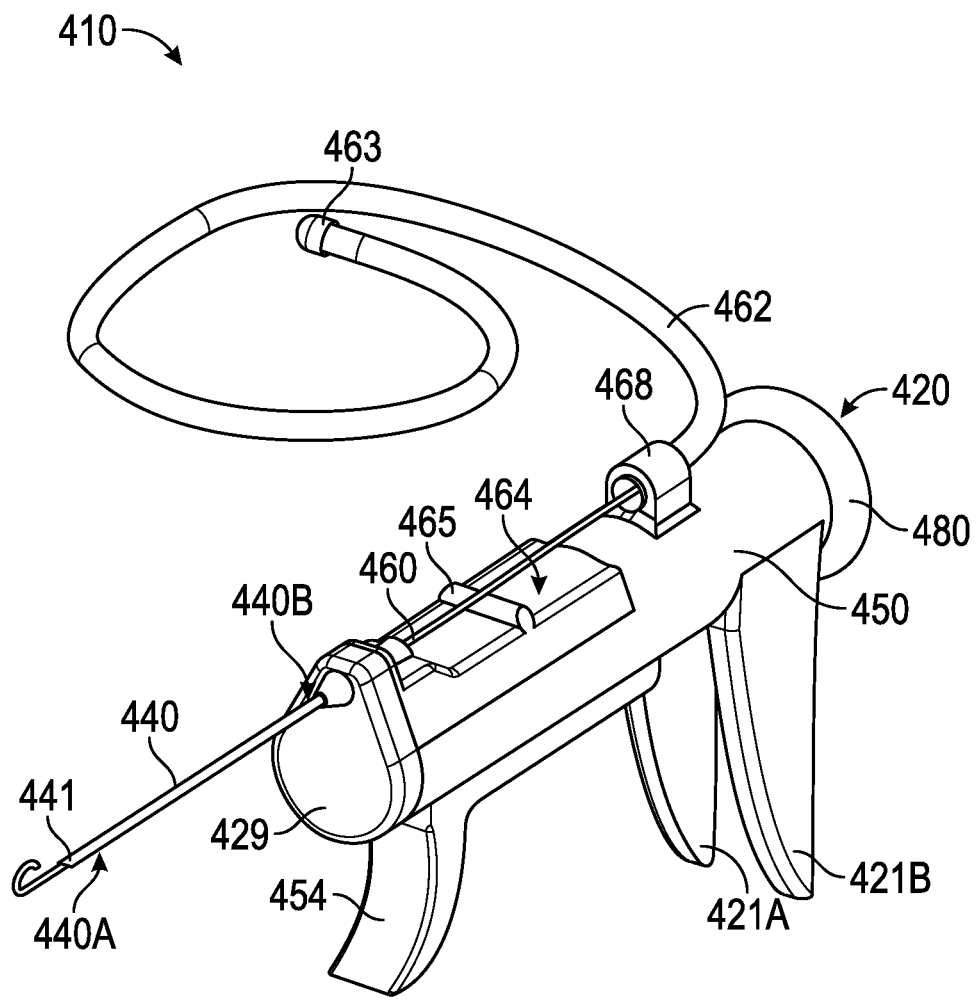
FIG. 19 illustrates a top perspective view of the insertion device in accordance with another embodiment.
Figure 20:
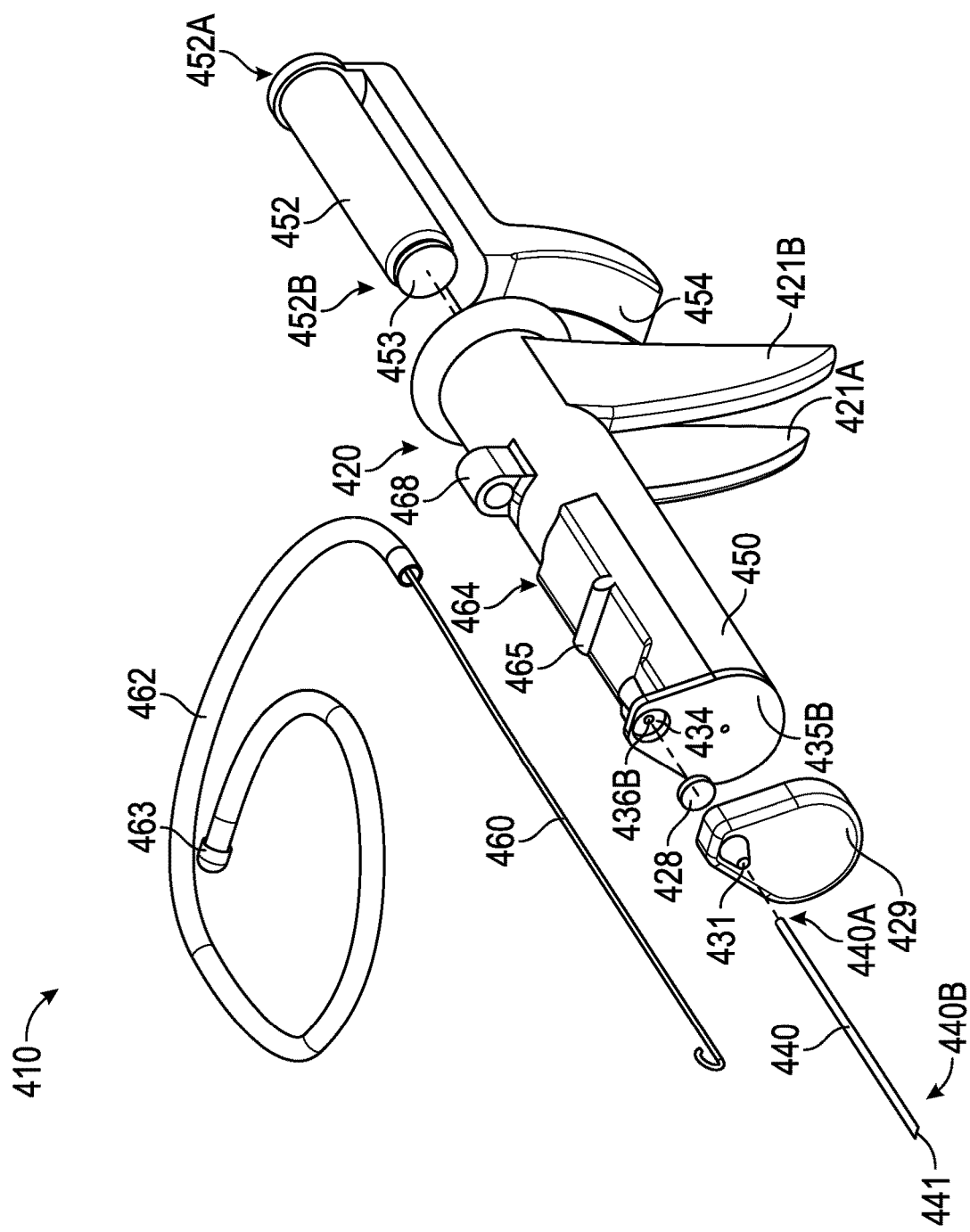
FIG. 20 illustrates a top perspective exploded view of the insertion device in accordance with the embodiment depicted in FIG. 19.
Figure 21:
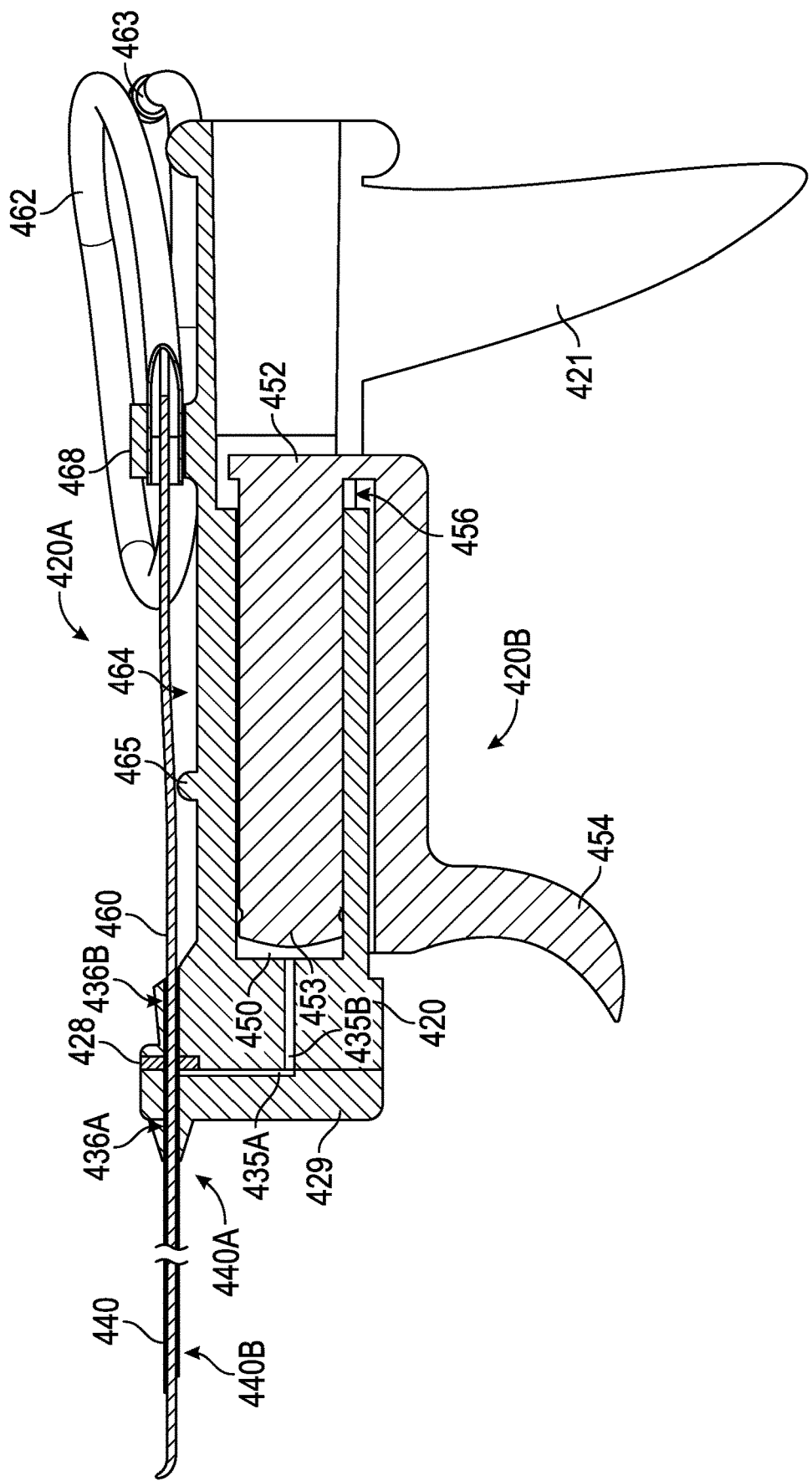
FIG. 21 illustrates a side cross-sectional view of the insertion device in accordance with the embodiment depicted in FIG. 19.

The embodiment depicted in FIGS. 19-21, like other embodiments disclosed herein, is configured to be used in either the right hand or the left hand of a clinician. As shown, insertion device 410 includes main housing 420. Main housing 420, for reference in the figures, has a top side 420A and a bottom side 420B. Main housing 420 includes handles 421A and 421B toward the proximal end of main housing 420, extending from bottom side 420B and main housing 420. Handles 421A and 421B are used to facilitate the gripping of insertion device 410 using a single hand. Typically, insertion device 410 is gripped using only the dominant hand of a clinician, or user, as will be described in more detail below. Handles 421A and 421B can be configured using a variety of arrangements. In this embodiment, handles 421A and 421B are preferably configured to allow the clinician to grip the distal end of handles 421A and 421B with the pinky, ring, and middle fingers of the dominant hand. In the present embodiment, main housing 420 is composed of thermoplastic such as polycarbonate and is substantially transparent. Construction of main housing 420 using material that is substantially transparent facilitates the visualization by the clinician of body fluids that are aspirated into various portions of main housing 420, as will be explained in further detail below. If main housing 420 is made of a substantially non-transparent material, such as a substantially translucent or substantially opaque thermoplastic, it may be desirable to include cut-out or other window-type areas in housing 420 to permit the clinician to visualize into various conduits (such as conduit 435A and 435B) and/or vacuum chamber 450 during use as will be explained in further detail below. The proximal end of main housing 420, in this embodiment, has a rounded end that may increase grip stability and comfort in the palm of the user.

Main housing 420 includes a main housing cap 429. Main housing cap 429 includes needle attachment opening 431, conduit 436A, and channel 435A. Main housing cap 429 is formed of substantially transparent thermoplastic such as polycarbonate. However, it will be recognized that main housing cap 429 may be formed of other materials as well, and may be translucent, substantially opaque, or opaque. In the event that main housing cap 429 is not formed of material that is substantially transparent, it may be desirable to form main housing cap 429 with a clear, or substantially transparent, section, such as a window, that would permit a user to visualize contents of channel 435A while insertion device 410 is in use, in particular to allow user to visualize the presence of fluid from the targeted body space in channel 435A while aspirating into vacuum chamber 450. In this embodiment, needle attachment opening 431 is continuous with conduit 436A, which runs through main housing cap 429. When main housing cap 329 is mounted onto main housing 420, conduit 436A in main housing cap 429 is contiguous with conduit 436B in main housing 420. Main housing cap 429 can be affixed to main housing 420 using a variety of suitable methods such as, for instance, ultrasonic welds, epoxy, or resin for a permanent attachment. It will be appreciated that main housing cap 429 may also be temporarily affixed to main housing 420 using clips, screws, or other suitable means. In an instance where main housing cap 429 is temporarily affixed to main housing 420, it will be recognized by a person of skill in the art that additional seals may be deployed to ensure that conduits 435A, 435B, 436A, and 436B are substantially air-tight during use such that the necessary pressure differential, as described herein, can be maintained to permit the aspiration of body fluids from the targeted body space.

A hollow piercing structure, such as needle 440, is included in insertion device 410. Proximal end 440A of needle 440 is affixed, through needle attachment opening 431 into conduit 436A of main housing cap 429. Various methods of affixing needle 440 to main housing cap 429 and main housing 420 will be appreciated, including plastic cement, appropriate epoxy, and ultraviolet cured cement. However, to practice the inventions disclosed herein, it is not necessary that needle 440 be permanently affixed to main housing cap 429 and/or main housing 420. Indeed, it will be appreciated that in some embodiments of the inventions disclosed herein, it may be desirable for needle 440 be to movably and/or removably attached to main housing cap 429 and/or main housing 420 so that, for example, needle 440 can be changed or for example, the orientation of needle 440 can be altered so that the direction of bevel 441 of needle 440 can be adjusted relative to the orientation of housing 420. Changes to the orientation of bevel 441 of needle 440 can be particularly useful when adapting insertion device 410 for ambidextrous use or for the personal preference of bevel 441 orientation of a clinician.

FIG. 17 depicts the proximal end 440A of needle 440 terminating within conduit 436A. It should be noted, however, that proximal end 440A of needle 440 could be extended into conduit 436B. With such a design, needle 440 should be configured so that the region around proximal end 440A of needle 440 includes an opening (not shown) along the shaft of needle 440 that is in communication with the lumen of needle 440. This opening on needle 440 is oriented to communicate with conduit 435A to permit the flow of aspirated body fluids from the region of the distal end 440B of needle 440, through the lumen of needle 440, and into conduit 435A. Such aspirated body fluids would be permitted to flow through conduit 435A into conduit 435B and ultimately into vacuum chamber 450.

Insertion device 410 further includes vacuum chamber 450 configured to receive plunger 452. Vacuum chamber 450 is in communication with conduits 435B and 435A such that pressure differential created in vacuum chamber 450 will create a suction passing through conduit 435 into the lumen of needle 440, to permit the aspiration of fluids through the distal end 440B of needle 440. Plunger 452 includes a proximal end 452A and a distal end 452B. Handle 454 is positioned adjacent to distal end 452B of plunger 452, and connected to proximal end 452A of plunger 452 by member 456 as shown in FIG. 16. Member 456 is offset from the sidewall of plunger 452 by a distance approximately equal to the thickness of the bottom wall of vacuum chamber 450 such that the space between the wall of plunger 452 and member 456 creates a channel into which the bottom side wall of vacuum chamber 450 can fit. In this way, plunger 452 can be drawn in a proximal direction by the proximal movement of handle 454. At least the top face of member 456 is shaped to match the exterior of housing 420 at the region of vacuum chamber 450. Member 456 is configured to support handle 454 so that handle 454 can be used to move plunger 452 in a proximal (and distal) direction, as well as to secure plunger 452 in vacuum chamber 450. Ring 420 can be attached to the proximal end of housing 420 to prevent the movement of plunger 452 out of the proximal end of vacuum chamber 450.

Insertion device 410 is further configured to include guidewire 460. In this embodiment, the proximal region of guidewire 460 is disposed within guidewire housing 462, which, in turn, is removably attached to main housing 420 at guidewire housing connector 468. Guidewire housing 462 may be either rigid or flexible, and may be permanently or removably attached to main housing 420. Further, as shown in the Figures, guidewire housing 462 may be configured to receive cap 463. Cap 463 can serve to retain guidewire 460 in guidewire housing 462, as well as to isolate guidewire 460 from potential contaminants in the surrounding environment.

Guidewire 460 spans guidewire feed region 464. Main housing 420 is configured to receive the distal end of guidewire 460 in conduit 436. In this embodiment, valve 428 is provided and configured to permit guidewire 460 to pass through it prior to entering conduit 436. As shown, valve 428 seated in valve seat 444 and held in place at least by main housing cap 429. Valve 428 is configured to allow guidewire 460 to pass through it prior to entering conduit 436B.

Valve 428 serves in insertion device 410 to prevent the substantial movement of air through conduit 436B such that the pressure differential created by the proximal movement of plunger 452 in vacuum chamber 450 would be defeated. Preferably, valve 428 would provide an air-tight seal around the guidewire of at least about 300 mmHg of pressure. However, it will be appreciated that the function of the inventions disclosed herein, and specifically the aspiration of fluid from a targeted body space through the lumen of needle 440 and ultimately into vacuum chamber 450, the inventions disclosed herein could be practiced with a vacuum of more or less than about 300 mmHg pressure, depending on the specific application and design of the insertion tool 410. It will also be apparent that valve 428 may not be necessary to maintain the necessary vacuum, if the entry to conduit 436B is sized so that the guidewire itself creates a sufficient seal to substantially prevent the flow of air through conduit 436B during aspiration.

When insertion tool 340 is prepared for use, it may be beneficial to use, depending on the specific application, that guidewire 460 is disposed within needle 440, with the distal end of guidewire 360 close to distal end 340B of needle 440. The tip of the distal end of guidewire 460, however, should not extend through the distal end 440B of needle 440, and should remain clear of bevel 441 of needle 440. However, when the distal tip of guidewire 460 is placed near the distal end 440B of needle 440 when insertion device 410 is prepared for use, the user is able to more rapidly advance guidewire 460 into the targeted body space, thus securing access to the targeted body space, as soon as puncture of the targeted body space is confirmed, such as through the aspiration of appropriate body fluids through conduit 435 and/or into vacuum chamber 450.

The insertion device 410 depicted in FIGS. 19-21 can be used to perform a venous access procedure using the ultrasound-guided modified Seldinger Technique, employing the inventions disclosed herein. When prepared for use, guidewire 460 may be positioned within conduit 436, with the distal end of guidewire 460 reasonably close to, but proximal to, tip 441 of needle 440. Such pre-positioning of guidewire 460 in the lumen of needle 440 can assist in the rapid deployment of guidewire 460 into the targeted body space. However, such pre-positioning of guidewire 460 within the lumen of needle 440 is not necessary for the practice of this method, or, guidewire 460 can be prepositioned so that the distal tip of guidewire 460 is distal to valve 428 or even proximal to valve 428.

A clinician grasps insertion device 410 in the dominant hand and an ultrasound probe (not shown) in the non-dominant hand. In particular, the clinician grasps housing 420 of insertion device 310 in the palm of the dominant hand with the pinky, ring, and middle fingers of the dominant hand grasping handles 421A and/or 421B. The index finger rests around or against grip 454, and the thumb rests against the guidewire feed region 464. The clinician presses the tip 441 of needle 440 against a patient's skin and uses it to penetrate through tissue. While the clinician is inserting the needle, the clinician uses the ultrasound probe and the image produced by the ultrasound machine to follow the progress of needle 440 as it pierces through the tissue. Also, while the clinician is inserting needle 440 through patient tissue, the clinician uses the index finger of the dominant hand to draw back plunger 352 using grip 354, thereby creating a suction in vacuum chamber 450.

The suction created in vacuum chamber 450 in turn results in a suction at tip 441 of needle 440 through conduit 435. Body fluid is drawn from the region around tip 441 of needle 440, through the needle lumen, through conduit 435 and into vacuum chamber 450. When the tip 441 of needle 440 accesses and pierces the targeted vein, blood flows through the lumen of needle 440, into conduit 435A and 435B and into vacuum chamber 450. Visualization of blood in conduit 435A, conduct 435B, and/or vacuum chamber 450 indicates to the clinician that the targeted vein has been reached and punctured. It will be appreciated that where this process is applied for the access of targeted body regions other than veins, the appearance of other, appropriate body fluids in conduit 435A, conduit 435B, and/or vacuum chamber 350 would indicate that the particular targeted body region had been reached.

Once the targeted body region, in this example the vein, has been reached, the clinician stops moving needle 440 forward. The clinician uses the thumb of the dominant hand to press guidewire 460 against protrusion 465 and advance guidewire 460 in a distal direction by repeatedly moving the thumb along the guidewire feed region 464 and over protrusion 465. As explained above, protrusion 465 may be easily replaced in some embodiments of the inventions disclosed herein with a wheel, button, or other structure in guidewire feed region 464 configured to aid the clinician in advancing guidewire 460 in a distal direction and/or retracting guidewire 460 in a proximal direction.

In this manner, the clinician uses the thumb to advance guidewire 460 in a distal direction, through conduit 436 and valve 428 into the lumen of needle 440, past the tip 441 of needle 440 and into the vein or other targeted body space. Because the access device allows for single-handed venipuncture and insertion, the operator can use ultrasound imaging to visualize the needle tip while it is inside of the vein and the guidewire as it is advanced into the vein.

Consequently, the risk of tissue injury diminishes. Furthermore, retaining ultrasound visibility allows the operator to ensure that the guidewire is going into the targeted vein as he inserts it. After the operator inserts the guidewire into the vein to the desired length, the access device is removed while the guidewire remains in place for dilation and catheter, sheath, or cannula insertion.

Data evaluating the efficacy of the inventions described herein has been collected in a preliminary study and indicate that the inventions described herein are efficacious for ultrasound guided central venous catheter ("CVC") insertion. An insertion device according to these inventions and generally corresponding to the embodiment described in FIGS. 5-7 was tested using the techniques and methods described herein.

Resident and attending physicians at an academic medical center were recruited to place a CVC catheter in a right internal jugular vein simulator mannequin using both (1) the standard ultrasound-guided Seldinger technique and CVC kit and (2) the insertion device and methods according to the inventions described herein (the "Invention"). Subjects were observed and timed on their placement of the CVC with each technique, total ultrasound visualization time, success of first cannulation, number of cannulation attempts, and arterial punctures recorded. At the conclusion of their testing they completed a survey on their experience with the insertion device and methods according to the inventions described herein. Continuous data such as time for each technique were compared used a paired Student's t-test, categorical data using a McNemar test, and ordinal data using a Wilcoxon signed rank test as appropriate.

Thirty-six subjects were recruited. Represented specialties included emergency medicine (44%), anesthesiology (33%), and surgery (22%) with a median postgraduate year (PGY) level 3. All subjects had previously been trained in CVC insertion and use of ultrasound with 80.6% having placed greater than fifteen CVCs. Additional details concerning the characteristics of the test subjects are provided in Table 1.

TABLE 1

| Characteristics | Subjects (n = 36) | % |
| --- | --- | --- |
| Age (years) | 31.4 | |
| Female | 15 | 41.7 |
| Specialty | | |
| EM | 16 | 44.4 |
| Anesthesia | 12 | 33.3 |
| Surgery | 8 | 22.2 |
| Postgraduate year (median) | 3 | |
| Previous CVC training | 36 | 100.0 |
| Previous US training | 36 | 100.0 |
| Previous CVCs placed | | |
| 0 | 0 | 0.0 |
| 1-3 | 0 | 0.0 |
| 4-6 | 3 | 8.3 |
| 7-9 | 2 | 5.6 |
| 10-12 | 1 | 2.8 |
| 12-14 | 1 | 2.8 |
| >15 | 29 | 80.6 |
| Confidence in placing CVCs (mean 5-point Likert scale) | 4.3 | |

Results of the study showed that mean total procedure time was significantly decreased in the Invention group (97 seconds versus 119 seconds, P<0.0001); mean percent ultrasound visualization time during the procedure was significantly increased using the Invention (31% versus 7%, P<0.0001). There were non-significant trends towards increased first cannulation attempt success (32 subjects versus 29 subjects, P=0.453), decreased venous cannulation attempts (5 subjects versus 3 subjects, P=0.470), and fewer arterial punctures (1 subject versus 0 subjects, P=0.317) when using the Invention. All subjects surveyed stated they would use Invention in a clinical setting, and 80.6% would prefer the Invention over a standard CVC kit. The results of the study are provided in Tables 2-4.

TABLE 2

| Result | Standard | Invention | P |
| --- | --- | --- | --- |
| Total Procedure Time (seconds) | 119 | 97 | <.0001 |
| Percent US Visualization (percent, %) | 7.2 | 31.1 | <.0001 |
| Success of first cannulation (subjects) | 29 | 32 | 0.453 |

TABLE 3

| Result | Frequency | % | P |
| --- | --- | --- | --- |
| Venous cannulation attempts | | | 0.470 |
| Fewer attempts with Invention | 5 | 13.9 | |
| Fewer attempts with standard | 3 | 8.3 | |
| Arterial punctures | | | 0.317 |
| Fewer arterial punctures with Invention | 1 | 2.8 | |
| Fewer arterial punctures with standard | 0 | 0.0 | |
| Would use Invention in clinical setting | 36 | 100.0 | |
| Would use Invention over standard | 29 | 80.6 | |

TABLE 4

| Result | 5-point Likert scale |
| --- | --- |
| Invention Ease of Use | 4.1 |
| Invention Ease of Use with US | 4.7 |
| Invention Ease of Use with Initial Access | 4.4 |
| Invention Ease of Use on Repeat Attempt | 4.4 |

Data from the study demonstrated that using the Invention is efficacious and feasible for ultrasound-guided CVC placement. It compares favorably to insertion with standard CVC kits and technique with regards to total procedure time and percent of the procedure under ultrasound visualization. It may allow for safer insertion with fewer venous cannulation attempts and arterial punctures. Despite this study being the first encounter with the Invention, subjects were comfortable with its use and expressed a general preference for it over standard methods.

Figure 22:
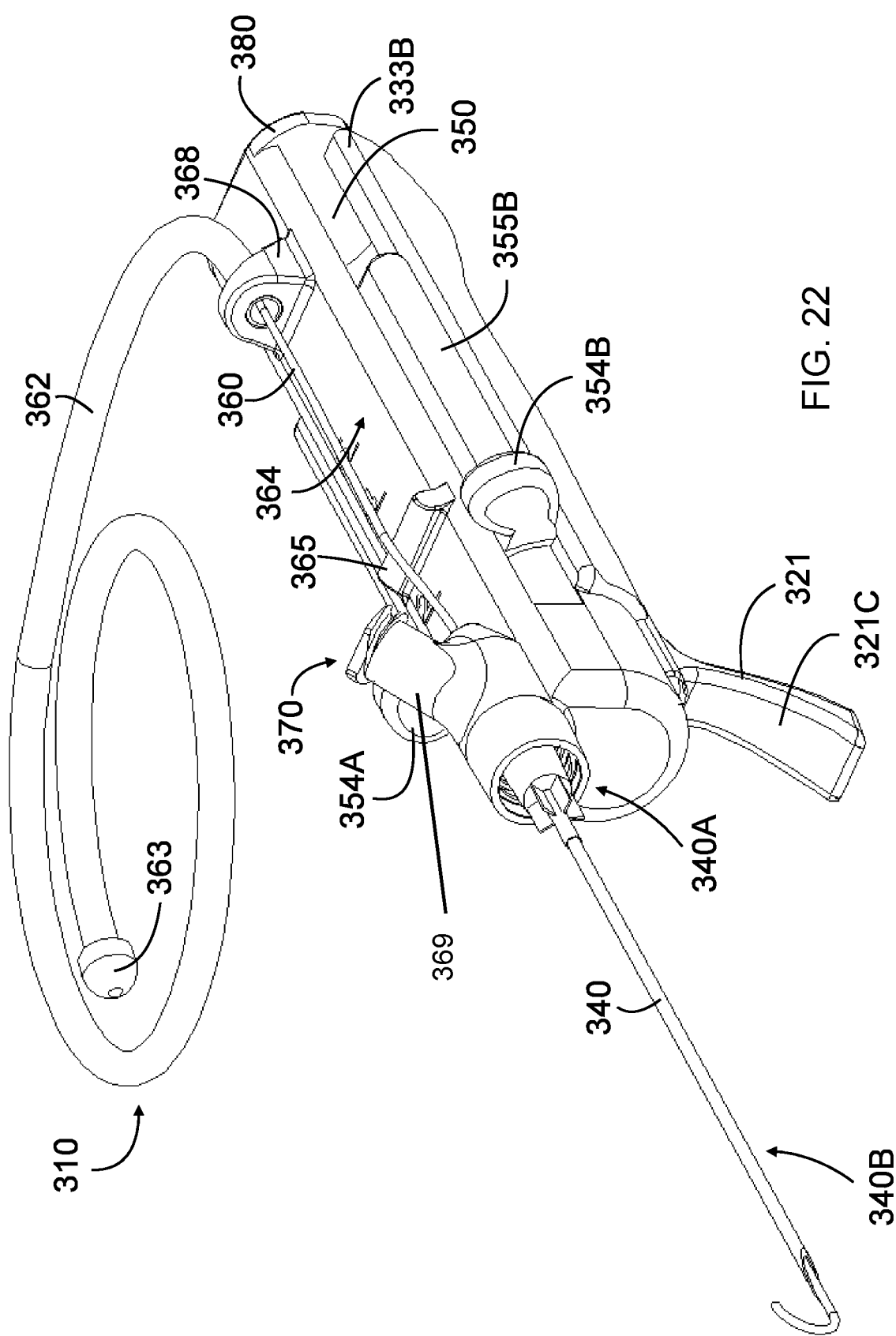
FIG. 22 illustrates an embodiment of the insertion devices disclosed herein comprising a pressure monitoring channel.
Figure 23:
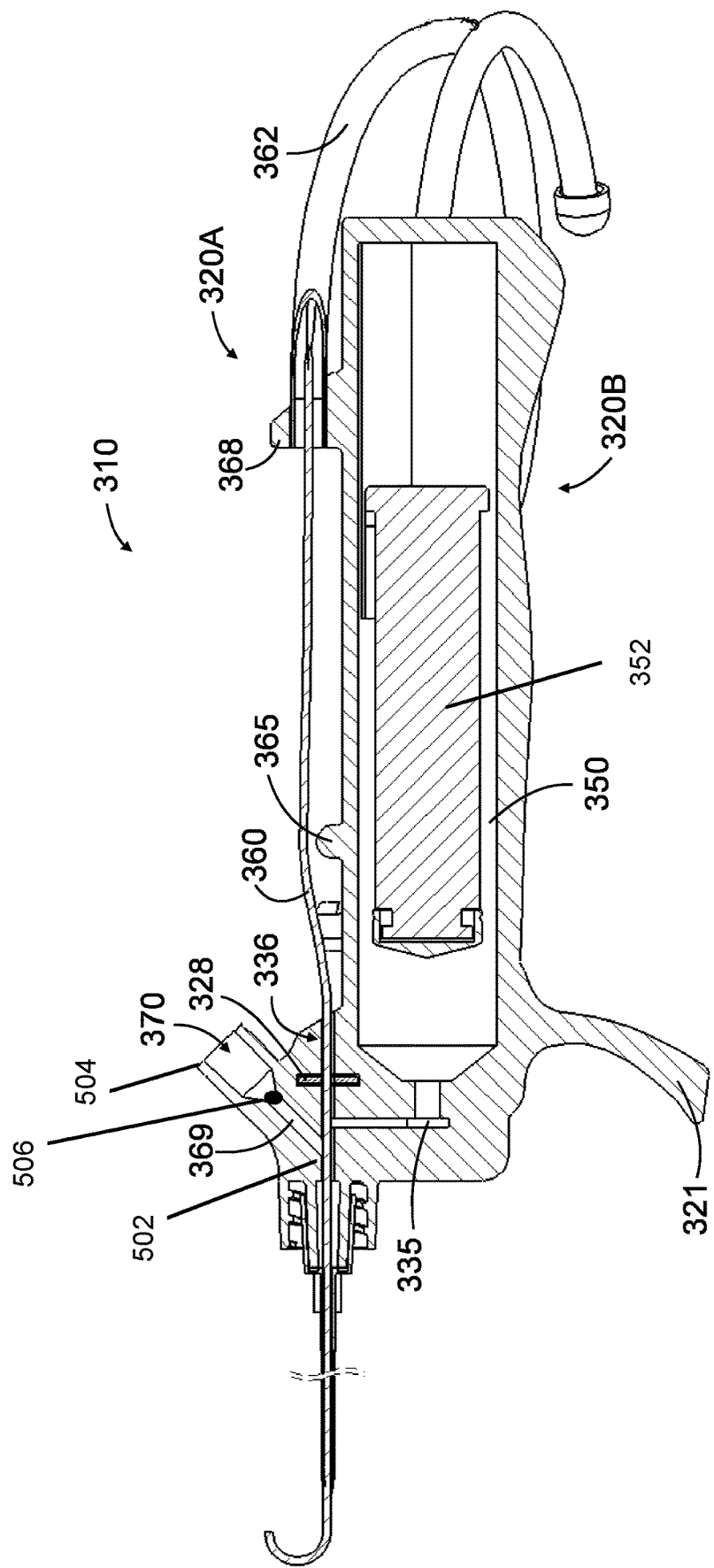
FIG. 23 illustrates a side cross-sectional view of the insertion device illustrated in FIG. 22.

Turning now to FIGS. 22 through 26, those of skill will appreciate that blood color and/or pulsatility may not be reliable indicators of proper placement of needle 340 in a body part; however, pressure verification, such as instantaneous pressure verification, typically is reliable. With this in mind, FIGS. 22 and 23 illustrate another embodiment of the present inventions previously described with the addition of a pressure channel 369. As clearly shown in FIG. 23, pressure channel 369 may comprise a first end 502 that communicates with the conduit 336 and/or 335, and preferably upstream of valve 328, and a second end 504. The second end 504 preferably comprises a leak free fitting structure 370, such as, but not limited to, a Luer-Lok connection for connecting the pressure-monitoring channel 369 to other structures and devices, such as described further below.

The pressure-monitoring channel 369 may be configured to convey the pressure state of the conduit 336 (and therefore the pressure state, or a representation of the pressure state, of the body part) to the second end 504 of the channel 369. The pressure state communicated by the channel 369 may be positive pressure (i.e., greater than ambient pressure) or negative pressure (i.e., less than ambient pressure). The pressure-monitoring channel 369 may be configured to convey only positive pressure to second end 504 through use a one-way or check valve 506. For example, when the plunger 352 is used to aspirate the body part (such as for blood draw back), the check valve 506 may be configured to prevent air or other fluids from being drawn into the conduit 336 from the second end of the pressure monitoring channel 369. Medical grade check or one-way valves such as those offered by Nordson Medical may be suitable for this purpose. In other embodiments, the check valve 506 may be omitted. In such embodiments without a check valve, fluids, such as saline, anti-coagulants, and other medicaments, may be drawn into the conduit 336 and/or 350 chamber during aspiration for injection into the body part.

Figure 24:
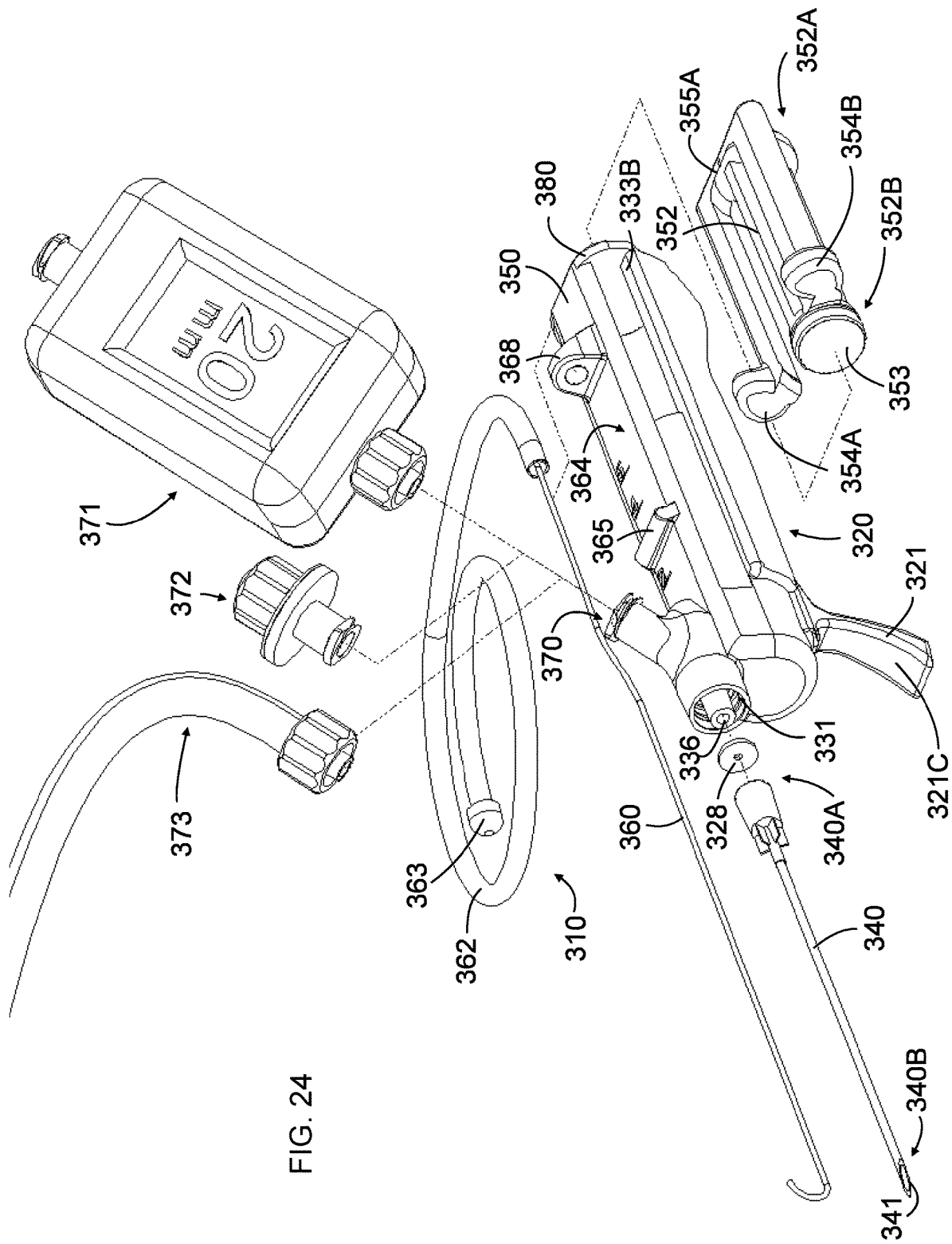
FIG. 24 illustrates the insertion device of FIG. 22 comprising additional pressure monitoring mechanisms coupled to the pressure-monitoring channel.

FIG. 24 illustrates an embodiment of the insertion device 310 in FIG. 22 along with other structures useful for transducing pressure via the pressure-monitoring channel 369. A cap 372 is illustrated as being connectible to the second end 504 of the pressure-monitoring channel 369, such as through the leak free connection 370. The cap 372 may be a blind cap, such that the cap 372 seals the pressure-monitoring channel to the outside environment. Alternately and/or optionally, the cap 372 may comprise a check valve or one-way valve to allow fluid from the conduit 336 to leak out of the cap at a predetermined pressure level, such as when an artery, rather than a vein, is accessed. Alternately and/or optionally, the cap 372 may comprise the check valve 506 described above. In this embodiment of the cap 372, the outer end of the cap 372 preferable comprises a leak free connection, such as described above, to which other structures may be attached. If the cap 372 comprises a check valve 506, the pressure-monitoring channel 369 need not also include a check valve, such as shown in FIG. 23.

Also shown in FIG. 24 is a digital pressure transducer 371, such as, but not limited to, the Compass digital pressure transducer offered by Centurion Medical Products. The pressure transducer 371 is illustrated as being connectible to the second end 504 of the pressure-monitoring channel 369, such as through the leak free connection 370. With this embodiment, once the pressure transducer 371 is coupled to the insertion device 310 via the leak free connection 370, the operator will have instantaneous, or near instantaneous, measurement, and readout of the conduit 336 pressure, if desired. Alternately or additionally, the pressure transducer 371 may be used to determine or visualize the pressure waveform of the accessed body part. It will be appreciated that the pressure waveform alone may permit determination of whether the body part accessed is, for example, an artery or a vein. In others words, measurement of the absolute pressure is not always necessary or desired.

As is known in the art, measurement of pressures in the venous system and the pulmonary vessels can play an important role in intensive care medicine. Venous pressure, the vascular pressure in a vein or in the atria of the heart, is much less than arterial pressure, with common values of 5 mmHg in the right atrium and 8 mmHg in the left atrium. Central venous pressure may be a good approximation of right atrial pressure, which may predict right ventricular end diastolic volume. The jugular venous pressure is the indirectly observed pressure over the venous system and can be useful in the differentiation of heart and lung diseases. The blood pressure in the portal vein is normally 5-10 mmHg. Thus, embodiments of the insertion device allowing real-time blood pressure and waveform monitoring may be useful not only for needle 340 placement, but for diagnostic and other purposes as well.

Also shown in FIG. 24, is pressure tube 373, which can oriented in a vertical direction to allow visual acquisition of the pressure waveform from the body part. For example, a venous or arterial blood column in the pressure tube may allow the operator to visualize the pressure waveform a make a determination of what type of body part has been accessed.

Embodiments of the insertion device 310 with a pressure monitoring channel 369 may also utilize a conventional pressure transducer, a digital manometer or a conventional manometer, connected to leak free connection 370 to the to permit the operator to monitor real time conduit (i.e., body part) pressure and/or visualize the pressure waveform.

Although not illustrated in FIG. 24, as described above, the pressure-monitoring channel also can function to allow fluids, such as medicaments, to be introduced into the body part such as by use of a conventional syringe or a drawdown bag. For example, and not limitation, after insertion of the needle 340 into the body part (such as a vein) and draw back confirming placement, a syringe or draw down bag containing medicament(s) may be attached to the leak free connection 370 of the pressure-monitoring channel 369. Additional draw back of the plunger 352 will draw the medicament into the chamber 350, which can then be injected into the body part prior to or during guide wire 360 placement. The syringe or draw down bag then can be removed and one of the several pressure structures described above can be attached to the leak free connection 370. Still further, those of skill will now appreciate how the pressure-monitoring channel 369 may be used to draw a blood sample.

Figure 25:
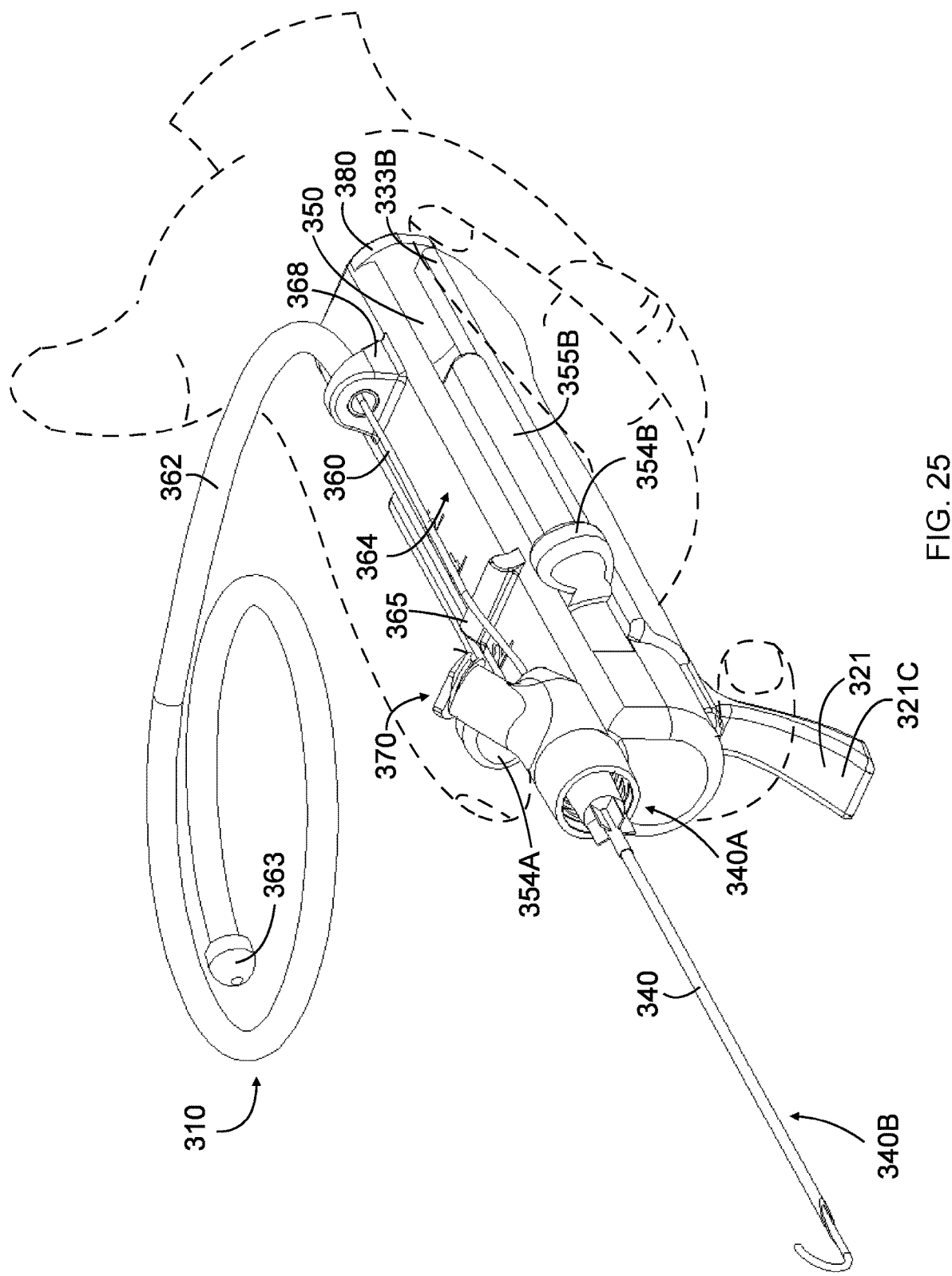
FIGS. 25 and 26 illustrate the insertion device of FIG. 22 during single-handed operation.
Figure 26:
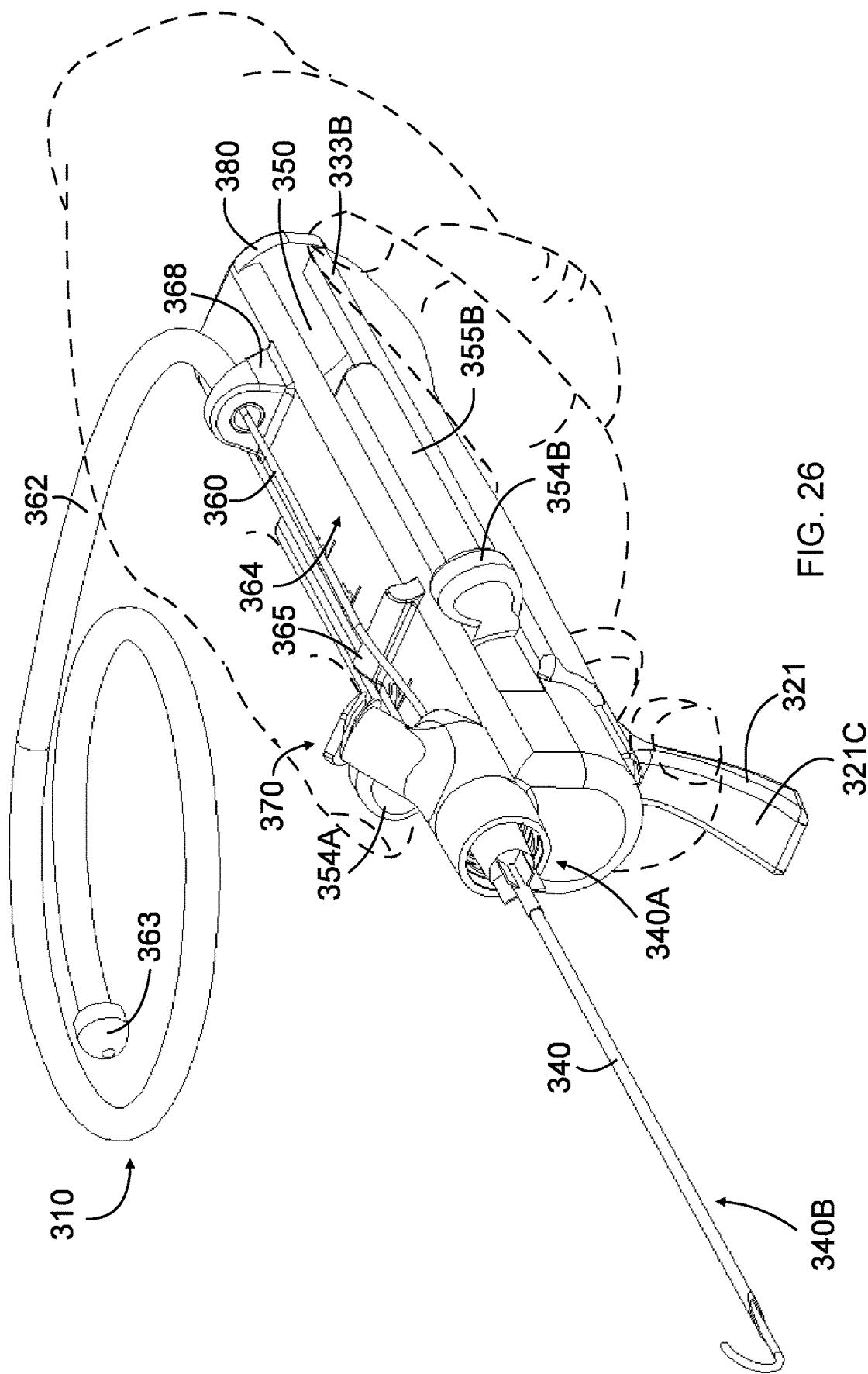

FIGS. 25 and 26 illustrate the insertion device of FIGS. 22-24 in single-handed operation prior to or after connection of pressure structures to the pressure-monitoring channel 369.

Those persons of skill having benefit of this disclosure will readily appreciate that the embodiments, components, and functionalities described and illustrated in FIGS. 1 through 26, can be mixed, matched, combined or eliminated to create many different embodiments of the insertion device suitable for a wide variety of procedures and purposes without departing from the spirit of the inventions disclosed herein.

Other and further embodiments utilizing one or more aspects of the inventions described above can be devised without departing from the spirit of Applicant's invention. For example, a device and method that facilitates one-handed insertion of not only the guidewire, but also the dilating and catheter components as well. Further, the various methods and embodiments of the insertion apparatus can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. A method of inserting an object into a body using an insertion apparatus, the insertion apparatus comprising a housing having a proximal end and a distal end, a first handle associated with the distal end of the housing, a piercing structure with a lumen, the piercing structure extending distally from the housing, a vacuum chamber in communication with the lumen of the piercing structure, a plunger associated with the vacuum chamber and configured to fit within moveable within the vacuum chamber, a plunger handle operatively connected to the plunger and disposed on an outer surface of the housing between the distal and proximal ends, the method comprising:
holding the insertion apparatus with a first hand with the proximal end of the housing engaging a palm of the first hand and the first handle engaging the index or middle finger of the first hand;
piercing a skin of a patient with the piercing structure while the proximal end of the housing engages the palm and the first handle engages the index or middle finger;
creating a pressure differential in the vacuum chamber by moving the plunger handle in a proximal direction away from the first handle using a finger or thumb of the first hand while the proximal end of the housing engages the palm and the first handle engages the index or middle finger;
advancing a guidewire through the lumen of the piercing structure using the thumb of the first hand while the proximal end of the housing engages the palm and the first handle engages the index or middle finger; and
monitoring pressure in the lumen via a pressure-monitoring channel in the insertion apparatus.

2. The method of claim 1, further comprising: confirming puncture of a targeted body space by a value of pressure in the lumen.

3. The method of claim 1, wherein monitoring pressure in the lumen comprises fitting a pressure cap to the pressure-monitoring channel, the pressure cap configured to leak fluid at a predetermined pressure.

4. The method of claim 1, wherein monitoring pressure in the lumen comprises a digital pressure transducer communicating with the pressure-monitoring channel.

5. The method of claim 1, wherein monitoring pressure in the lumen comprises a digital pressure transducer communicating with the pressure-monitoring channel, and further comprising reading a pressure value from a visual display associated with the transducer.

6. The method of claim 1, further preventing fluid from the pressure-monitoring channel from being drawn into the lumen by a one-way check valve in the pressure-monitoring channel.

7. The method of claim 1, wherein moving the plunger further comprises not moving the plunger handle beyond the proximal end of the housing.

8. The method of claim 7, wherein digits of the first hand contacting the first handle, the plunger handle, and guidewire, respectively, are selected from the group consisting of: a) middle finger, index finger and thumb; b) middle finger, thumb, and thumb; and c) index finger, thumb, and thumb.

9. The method of claim 1, wherein advancing the guidewire comprises sliding the guidewire against a protrusion on the housing with the thumb of the first hand.

10. The method of claim 1, wherein advancing the guidewire through the lumen comprises advancing the guidewire through a valve disposed proximally to the piercing structure.

11. A method of inserting an object, comprising:
providing an insertion apparatus having a housing with a proximal end and a distal end, a first handle associated with the distal end, a needle defining a lumen extending distally from the housing, a chamber in communication with the lumen configured to hold a vacuum, a plunger associated with the chamber, at least one second handle outside the housing disposed between the proximal and distal ends and operatively coupled to the plunger, the plunger configured to slide within the chamber to create a vacuum, a guidewire channel in communication with the lumen, and a pressure channel in communication with the lumen;
holding the insertion apparatus in a first hand with the proximal end contacting a palm and the first handle contacting a middle or index finger;
piercing the skin of a patient with the needle while holding the insertion apparatus in the first hand with the proximal end contacting the palm and the first handle contacting the middle or index finger;
drawing a vacuum in the chamber by sliding the second handle in a proximal direction between the proximal and distal ends and away from the first handle using a finger or thumb of the first hand while holding the insertion apparatus in the first hand with the proximal end contacting the palm and the first handle contacting the middle or index finger.

12. The method of claim 11, further comprising: confirming puncture of a targeted body space by a level of pressure in the lumen.

13. The method of claim 11, further comprising: fitting a pressure cap to the pressure channel, the pressure cap configured to leak fluid from the pressure channel at a predetermined pressure.

14. The method of claim 11, further comprising: fitting a digital pressure transducer to the pressure channel.

15. The method of claim 11, further comprising: fitting a digital pressure transducer to the pressure channel; and reading a pressure value from a visual display associated with the transducer.

16. The method of claim 11, further comprising: preventing fluid from the pressure channel from being drawn into the lumen by a one-way check valve in the pressure channel.

17. The method of claim 11, further comprising: contacting the at least one plunger handle associated with the plunger with the index finger or thumb of the first hand to slide the plunger.

18. An insertion device for a medical procedure, comprising:
a housing having a proximal end and a distal end;
a first handle associated with the distal end of the housing;

a piercing structure having a lumen, the piercing structure extending distally from the housing;

a plunger operatively associated with a vacuum chamber, which the vacuum chamber communicates with the lumen, and the plunger is moveable relative to the housing and the vacuum chamber;

a plunger handle operatively connected to the plunger, the plunger handle disposed outside the housing between the distal end and the proximal end and having a range of movement between the proximal end and the distal end not extending beyond the proximal end of the housing;

wherein the insertion device can be held by a first hand of an operator with the proximal end of the housing contacting a palm of the first hand, and an index or middle finger of the first hand contacting the first handle; and while being held in such manner, the piercing structure can be inserted into a body, and a vacuum drawn by moving the plunger handle toward the proximal end of the housing away from the first handle with a finger or thumb of the first hand.

19. The insertion device of claim 18, further comprising:

a guidewire channel within the housing and communicating with the lumen;

the guidewire channel having an opening on an outer surface of the housing; and a guidewire protrusion located between the guidewire channel opening and the proximal end of the housing for advancing a guidewire into the lumen with a thumb or finger of the first hand.

20. The insertion device of claim 19, further comprising:

a pressure channel within the housing communicating with the lumen; and the pressure channel having an opening located between the distal end and the proximal end of the housing.

\* \* \* \* \*